US006309663B1

(12) United States Patent
Patel et al.

(10) Patent No.: US 6,309,663 B1
(45) Date of Patent: Oct. 30, 2001

(54) TRIGLYCERIDE-FREE COMPOSITIONS AND METHODS FOR ENHANCED ABSORPTION OF HYDROPHILIC THERAPEUTIC AGENTS

(75) Inventors: Mahesh V. Patel; Feng-Jing Chen, both of Salt Lake City, UT (US)

(73) Assignee: Lipocine Inc., Salt Lake City, UT (US)

( * ) Notice: Subject to any disclaimer, the term of this patent is extended or adjusted under 35 U.S.C. 154(b) by 0 days.

(21) Appl. No.: 09/375,636

(22) Filed: Aug. 17, 1999

(51) Int. Cl.$^7$ .................................................. A61K 9/127
(52) U.S. Cl. ...................... 424/450; 424/451; 424/455; 424/456; 424/463; 424/489; 424/499; 424/502; 424/435; 424/464; 514/937; 514/938; 514/939; 514/940; 514/941; 514/942; 514/943; 514/975
(58) Field of Search .................................. 424/450, 451, 424/455, 456, 463, 489, 499, 502, 435, 464; 514/937–943, 975

(56) References Cited

U.S. PATENT DOCUMENTS

| | | |
|---|---|---|
| 4,388,307 | 6/1983 | Cavanak ................................ 424/177 |
| 4,572,915 | 2/1986 | Crooks .................................. 514/458 |
| 4,713,246 | 12/1987 | Begum et al. ....................... 424/455 |
| 4,719,239 | 1/1988 | Muller et al. ........................ 514/785 |
| 4,727,109 | 2/1988 | Schmidt et al. ..................... 424/455 |
| 4,944,949 | 7/1990 | Story et al. ......................... 424/451 |
| 4,994,439 | 2/1991 | Longenecker et al. ................ 514/3 |
| 5,071,643 | 12/1991 | Yu et al. ............................. 514/570 |
| 5,120,710 | 6/1992 | Liedtke ................................... 514/3 |
| 5,145,684 | 9/1992 | Liversidge et al. ................. 424/489 |
| 5,206,219 | 4/1993 | Desai ..................................... 514/3 |
| 5,244,925 | 9/1993 | Wretlind et al. .................... 514/777 |
| 5,342,625 | 8/1994 | Hauer et al. ........................ 424/455 |
| 5,350,741 | 9/1994 | Takada ................................... 514/3 |
| 5,364,632 | 11/1994 | Benita et al. ....................... 424/450 |
| 5,444,041 | 8/1995 | Owen et al. ........................... 514/2 |
| 5,532,002 | 7/1996 | Story .................................. 424/456 |
| 5,589,455 | 12/1996 | Woo ..................................... 514/11 |
| 5,614,491 | 3/1997 | Walch et al. ......................... 514/11 |
| 5,616,330 | 4/1997 | Kaufman et al. ................... 424/400 |
| 5,622,721 | 4/1997 | Dansereau et al. ................. 424/490 |
| 5,626,869 | 5/1997 | Nyqvist et al. ..................... 424/450 |
| 5,633,226 | 5/1997 | Owen et al. ........................... 514/2 |
| 5,639,474 | 6/1997 | Woo ..................................... 424/452 |
| 5,639,724 | 6/1997 | Cavanak .............................. 514/11 |
| 5,646,109 | 7/1997 | Owen et al. ........................... 514/2 |
| 5,653,987 | 8/1997 | Modi et al. ......................... 424/400 |
| 5,656,277 | 8/1997 | Berlati et al. ...................... 424/400 |
| 5,656,289 | 8/1997 | Cho et al. ........................... 424/455 |
| 5,665,379 | 9/1997 | Herslöf et al. ..................... 424/455 |
| 5,686,105 | 11/1997 | Kelm et al. ......................... 424/452 |
| 5,707,648 | 1/1998 | Yiv ...................................... 424/450 |
| 5,731,355 | 3/1998 | Jones et al. ........................ 514/731 |
| 5,741,822 | 4/1998 | Yesair ................................. 514/784 |
| 5,747,066 | 5/1998 | Pittrof et al. ...................... 424/450 |
| 5,766,629 | 6/1998 | Cho et al. ........................... 424/455 |
| 5,858,398 * | 1/1999 | Cho .................................... 424/450 |
| 5,858,401 | 1/1999 | Bhalani et al. .................... 424/450 |

OTHER PUBLICATIONS

Alvarez, F. J. and Stella, V. J., "The Role of Calcium Ions and Bile Salts on the Pancreatic Lipase–Catalyzed Hydrolysis of Triglyceride Emulsions Stabilized with Lecithin", *Pharmaceutical Research*, 6(6), 449–457 (1989).

Baluom, Muhammad, et al., "The Importance of Intestinal Residence Time of Absorption Enhancer on Drug Absorption and Implication on Formulative Considerations", *International Journal of Pharmaceutics*, 176, 21–30 (1998).

Bates, T. R. and Sequeira, J.A., "Bioavailability of Micronized Griseofulvin from Corn Oil–in–Water Emulsion, Aqueous Suspension, and Commercial Tablet Dosage Forms in Humans", *Journal of Pharmaceutical Sciences*, 64(5), 793–797 (1975).

Bernkop–Schnürch, Andreas, "The Use of Inhibitory Agents to Overcome the Enzymatic Barrier to Perorally Administered Therapeutic Peptides and Proteins," *Journal of Controlled Release*, 52, 1–16 (1998).

Charman, W. N., et al., "Physicochemical and Physiological Mechanisms for the Effects of Food on Drug Absorption: The Role of Lipids and pH", *Journal of Pharmaceutical Sciences*, 86(3), 269–282 (1997).

Gennaro, A. R., *Remington's Pharmaceutical Sciences*, Chapter 20, 293–300 (1985).

Hörter, D. and Dressman, J.B., "Influence of Physicochemical Properties on Dissolution of Drugs in the Gastrointestinal Tract", *Advanced Drug Delivery Reviews 25*, 3–14 (1997).

Johnson, L. R., "Gastrointestinal Physiology", *C. V. Morby Co., St. Louis*, Houston, Texas, 25–26, 93, 106, 133–134, 136–137 (1997).

LeCluyse, Edward L.; Sutton, Steven C., "In Vitro Models for Selection of Development Candidates. Permeability Studies to Define Mechanisms of Absorption Enhancement", *Advanced Drug Delivery Reviews*, 23, 163–183 (1997).

(List continued on next page.)

Primary Examiner—Thurman K. Page
Assistant Examiner—Lakshmi Channavajjala
(74) Attorney, Agent, or Firm—Dianne E. Reed; Reed & Associates

(57) ABSTRACT

The present invention relates to pharmaceutical compositions, pharmaceutical systems, and methods for enhanced absorption of hydrophilic therapeutic agents. Compositions and systems of the present invention include an absorption enhancing carrier, where the carrier is formed from a combination of at least two surfactants, at least one of which is hydrophilic. A hydrophilic therapeutic agent can be incorporated into the composition, or can be co-administered with the composition as part of a pharmaceutical system. The invention also provides methods of treatment with hydrophilic therapeutic agents using these compositions and systems.

170 Claims, No Drawings

OTHER PUBLICATIONS

MacGregor, K. J. et al., "Influence of Lipolysis on Drug Absorption From the Gastro–intestinal Tract", *Advanced Drug Delivery Reviews 25*, 33–46 (1997).

Pouton, C. W., "Formulation of Self–Emulsifying Drug Delivery Systems", *Advanced Drug Delivery Reviews 25*, 47–58 (1997).

Reymond, J. and Sucker, H., "In Vitro Model for Ciclosporin Intestinal Absorption in Lipid Vehicles", *Pharmaceutical Research*, 5(10), 673–676.

Tarr, D. T. and Yalkowsky, S. H. "Enhanced Intestinal Absorption of Cyclosporine in Rats Through The Reduction of Emulsion Droplet Size", *Pharmaceutical Research*, 6(1), 40–43 (1989).

Wilson, C. G., O'Mahony, B., "The Behaviour of Fats and Oils in the Upper G.I. Tract", *Bulletin Technique Gattefossé*, N° 90, 13–18 (1997).

Winne, D., "Dependence of Intestinal Absorption in Vivo on the Unstirred Layer", *Archives of Pharmacology*, 304, 175–181 (1978).

Zhi, J., Rakhit, A. et al., "Effects of Dietary Fat on Drug Absorption", *Clinical Pharmacology and Therapeutics*, 58(5), 487–491 (1995).

* cited by examiner

TRIGLYCERIDE-FREE COMPOSITIONS AND METHODS FOR ENHANCED ABSORPTION OF HYDROPHILIC THERAPEUTIC AGENTS

FIELD OF THE INVENTION

The present invention relates to drug, nutrient and diagnostic agent delivery systems, and in particular to pharmaceutical systems and methods for the improved delivery and enhanced absorption of hydrophilic therapeutic agents.

BACKGROUND

Hydrophilic therapeutic agents present difficult problems in formulation. While these therapeutic agents are readily soluble in water, and are easily dissolved in the gastrointestinal environment, simple dissolution is not sufficient to provide efficient bioabsorption of the therapeutic agent. Barriers to absorption are presented by the mucous layer, the intestinal epithelial cell membrane, and the junctional structure such as tight junctions between the epithelial cells. Due to the presence of the negatively charged mucosal layer, significant electrostatic binding or repulsion of charged molecules can be encountered. The epithelial cell membranes are composed of phospholipid bilayers in which proteins are embedded via the hydrophobic segments. These bilayers at the apical and/or basolateral cell surface represent very strong barriers for transport of hydrophilic substances, including peptides and proteins. Frequently, hydrophilic therapeutic agents are also subject to enzymatic attack and are degraded before they can be presented to the absorption site.

Some hydrophilic drugs such as acyclovir, foscarnet, tiludronate, pamidronate, alendronate, acarbose, cromolyn sodium, aminoglycoside and cephalosporin antibiotics are poorly absorbed from the gastro-intestinal tract, due to their low octanol-water partition coefficient, charge, and/or size.

Large water-soluble polymers, such as peptides, proteins, genetic material, vaccines and oligonucleotides, are not well absorbed from the intestine, primarily due to their low membrane permeability and enzymatic inactivation. The mammalian body possesses several efficient mechanisms to restrict the entry of macromolecules. These mechanisms include the presence of significant levels of enzymatic activity at various locations prior to entry into systemic circulation.

Thus, numerous barriers to absorption of hydrophilic therapeutic agents are present, and these barriers inhibit the effective absorption both of small hydrophilic therapeutic agents, such as conventional non-peptidic drugs, and of macromolecular hydrophilic therapeutic agents, such as proteins, peptides, vaccines and the like.

Much effort has been expended to develop methods of overcoming these absorption barriers. For example, the enzymatic barrier can be attacked by administering enzyme inhibitors to prevent or at least lessen the extent of presystemic degradation in the gastrointestinal tract (see, e.g., Bernkop-Schnurch, "The use of inhibitory agents to overcome the enzymatic barrier to perorally administered therapeutic peptides and proteins", *Journal of Controlled Release*, 52, 1–16 (1998)). Other efforts have focused on, for example, the use of absorption promoters to enhance epithelial permeability (e.g., LeCluyse and Sutton, "In vitro models for selection of development candidates. Permeability studies to define mechanisms of absorption enhancement", *Advanced Drug Delivery Reviews*, 23, 163–183 (1997)). However, the effectiveness of absorption enhancers such as permeability enhancers or enzyme inhibitors depends upon the ability of a pharmaceutical carrier to effectively present the absorption enhancers and the hydrophilic therapeutic agent to the absorption site, and prior efforts have not provided carriers which can do so efficiently. Moreover, maintaining effective carrier concentrations at the epithelium is not easily controlled in vivo. Too little carrier, or carrier concentrations only briefly maintained, may be ineffective. Too much carrier, or carrier concentrations maintained for too long, may result in compromised safety.

Frequently, carrier compositions for hydrophilic therapeutic agents include or are based on triglycerides. For example, U.S. Pat. Nos. 5,444,041, 5,646,109 and 5,633,226 to Owen et al. are directed to water-in-oil ("w/o") microemulsions for delivering water-soluble biological actives, such as proteins or peptides. The water-in-oil microemulsions convert into oil-in-water ("o/w") emulsions upon ingestion. The active agent is initially stored in the internal water phase of the w/o microemulsion, and is released when the composition converts to an o/w emulsion upon mixing with bodily fluids. Other oil-based or oil-containing formulations are taught in, for example, U.S. Pat. No. 5,120,710 to Liedtke, U.S. Pat. No. 5,656,289 to Cho et al. These triglyceride-containing formulations, however, suffer form several disadvantages.

U.S. Pat. No. 5,206,219 to Desai, for example, teaches compositions having a particle size of 5 to 50 microns. Typically, emulsions formed from triglyceride-containing compositions contain colloidal oil particles which are relatively large, ranging from several hundred nanometers to several microns in diameter, in a broad particle size distribution. Since the particle sizes are on the order of or greater than the wavelength range of visible light, such emulsions, when prepared in an emulsion dosage form, are visibly "cloudy" or "milky" to the naked eye. Emulsions are thermodynamically unstable, and colloidal emulsion particles will spontaneously agglomerate, eventually leading to complete phase separation. The tendency to agglomerate and phase separate presents problems of storage and handling, and increases the likelihood that pharmaceutical emulsions initially properly prepared will be in a less optimal, less effective, and poorly-characterized state upon ultimate administration to a patient. Uncharacterized degradation is particularly disadvantageous, since increased particle size slows the rate of transport of the colloidal particle and digestion of the oil component, and hence the rate and extent of absorption of the therapeutic agent. These problems lead to poorly-characterized and potentially harmful changes in the effective dosage received by the patient, and/or the rate of drug uptake. Moreover, changes in colloidal emulsion particle size are also believed to render absorption more sensitive to and dependent upon conditions in the gastrointestinal tract, such as pH, enzyme activity, bile components, and stomach contents. Such uncertainty in the rate and extent of ultimate absorption of the therapeutic agent severely compromises the medical professional's ability to safely administer therapeutically effective dosages. In addition, when such compositions are administered parenterally, the presence of large particles can block blood capillaries, further compromising patient safety.

U.S. Pat. No. 5,626,869 to Nyqvist et al. discloses compositions that would likely produce discrete lipid particles of relatively large size in vivo. Such particles suffer from the disadvantages of large size and low diffusivity, and are unable to effectively present any absorption enhancing components to the site of absorption.

A further disadvantage of conventional triglyceride-containing compositions is the dependence of therapeutic agent absorption on the rate and extent of lipolysis. Ultimately the triglyceride must be digested and the therapeutic agent must be released in order to be absorbed through the intestinal mucosa. The triglyceride carrier is emulsified by bile salts and hydrolyzed, primarily by pancreatic lipase. The rate and extent of lipolysis, however, are dependent upon several factors that are difficult to adequately control. For example, the amount and rate of bile salt secretion affect the lipolysis of the triglycerides, and the bile salt secretion can vary with stomach contents, with metabolic abnormalities, and with functional changes of the liver, bile ducts, gall bladder and intestine. Lipase availability in patients with decreased pancreatic secretory function, such as cystic fibrosis or chronic pancreatitis, may be undesirably low, resulting in a slow and incomplete triglyceride lipolysis. The activity of lipase is pH dependent, with deactivation occurring at about pH 3, so that the lipolysis rate will vary with stomach contents, and may be insufficient in patients with gastric acid hyper-secretion. Moreover, certain surfactants commonly used in the preparation of pharmaceutical emulsions, such as polyethoxylated castor oils, may themselves act as inhibitors of lipolysis.

Other carrier formulations avoid the use of triglycerides, but still suffer disadvantages. For example, U.S. Pat. No. 5,653,987 to Modi et al. is directed to pharmaceutical formulations for oral or nasal delivery of proteinaceous pharmaceutical agents using small amounts of particular surfactants and a protease inhibitor in an aqueous medium as absorption enhancers. However, in the gastrointestinal tract, where the volume of liquids is large and motility is great, polar drugs and the protease inhibitor are diluted even further upon administration, thus negating any potential benefits, since the composition is unable to deliver meaningful amounts of the absorption enhancers and pharmaceutical agents to the absorption site.

Thus, there is a need for pharmaceutical compositions that overcome the limitations of conventional formulations, to provide effective delivery of absorption enhancers and enhanced absorption of hydrophilic therapeutic agents.

SUMMARY OF THE INVENTION

It is therefore an object of the present invention to provide pharmaceutical systems capable of efficiently presenting hydrophilic therapeutic agents and absorption enhancing components to the absorption site.

It is another object of the present invention to provide pharmaceutical systems for delivery of a hydrophilic therapeutic agent that are not dependent upon lipolysis for bioabsorption.

It is another object of the present invention to provide pharmaceutical systems capable of increasing the rate and/or extent of bioabsorption of hydrophilic therapeutic agents.

In accordance with these and other objects and features, the present invention provides triglyceride-free pharmaceutical systems for enhanced bioabsorption of hydrophilic therapeutic agents. It has been surprisingly found that pharmaceutical compositions having absorption enhancing properties can be provided by using a combination of surfactants in amounts such that when the pharmaceutical composition is mixed with an aqueous diluent, an aqueous dispersion having a very small average particle size is formed. Such compositions can be co-administered with a hydrophilic therapeutic agent to increase the rate and/or extent of bioabsorption of the hydrophilic therapeutic agent, or can be provided with a hydrophilic therapeutic agent in the preconcentrate composition or in a diluent solution.

In one embodiment, the present invention relates to triglyceride-free pharmaceutical systems having a dosage form of an absorption enhancing composition comprising at least two surfactants, at least one of which is hydrophilic, and a hydrophilic therapeutic agent The surfactants are present in amounts such that the carrier forms an aqueous dispersion having a very small average particle size upon mixing with an aqueous diluent. The hydrophilic therapeutic agent can be solubilized, suspended, or partially solubilized and suspended, in the absorption enhancing carrier. Alternatively, the hydrophilic therapeutic agent can be provided separately, for co-administration with the dosage form of the absorption enhancing composition.

In another embodiment, the present invention provides a triglyceride-free pharmaceutical system for enhanced absorption of a hydrophilic therapeutic agent, including a dosage form of an absorption enhancing composition, and a hydrophilic therapeutic agent, wherein the absorption enhancing composition has at least one hydrophilic surfactant and at least one hydrophobic surfactant. The surfactants are present in amounts such that the carrier forms an aqueous dispersion having a very small average particle size upon mixing with an aqueous diluent. The hydrophilic therapeutic agent can be solubilized, suspended, or partially solubilized and suspended, in the dosage form of the absorption enhancing composition, or provided in a separate dosage form.

In another embodiment, the present invention provides a method of improving the bioabsorption of a hydrophilic therapeutic agent administered to a patient. The method includes the steps of providing a dosage form of an absorption enhancing composition, providing a hydrophilic therapeutic agent, and administering the dosage form of the absorption enhancing composition and the hydrophilic therapeutic agent to a patient. The method improves bioabsorption by improving the consistency of delivery of the hydrophilic therapeutic agent to the absorption site, and providing absorption enhancers at the absorption site.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention overcomes the problems described above characteristic of conventional formulations of hydrophilic therapeutic agents by providing unique pharmaceutical systems for enhanced absorption of hydrophilic therapeutic agents. The pharmaceutical systems include absorption-enhancing components which, when the compositions are mixed with an aqueous diluent either in vitro or in vivo, form aqueous dispersions having a very small particle size. The combination of absorption enhancing compounds at relatively high concentration, very small particle sizes upon dispersion, and the absence of triglycerides unexpectedly enhances the rate, extent and/or consistency of bioabsorption of hydrophilic therapeutic agents present in, or co-administered with, the absorption enhancing compositions.

The term "absorption enhancement" as used herein means an improvement in one or more of the rate of bioabsorption, the extent of bioabsorption, and the consistency of the rate and/or extent of bioabsorption. Without wishing to be bound by theory, it is believed that the absorption enhancement provided by the pharmaceutical systems of the present invention is a result of one or more of the following factors:

(1) effective presentation of an absorption enhancer to the site of enhancement;

(2) modulation of facilitated/active transport;

(3) transcellular permeability enhancement through favorable membrane perturbations;

(4) inhibition of efflux related transporters;

(5) inhibition of lumenal or cellular enzymatic inactivation;

(6) paracellular transport enhancement through loosening of tight junctions;

(7) induction of specific transporters to facilitate transport;

(8) altered biological binding characteristics;

(9) reduced degradation of the hydrophilic therapeutic agent;

(10) induction of transient water channels; and/or

(11) increased partitioning of the hydrophilic therapeutic agent by association with the absorption enhancer.

A. Pharmaceutical Compositions and Methods

In one embodiment, the present invention provides a triglyceride-free pharmaceutical system including an absorption enhancing composition. The absorption enhancing composition includes at least two surfactants, at least one of which is a hydrophilic surfactant. Preferably, the carrier includes at least one hydrophilic surfactant and at least one hydrophobic surfactant. The surfactants are present in amounts such that upon dilution with an aqueous diluent, either in vitro or in vivo, the carrier forms an aqueous dispersion having a small average particle size. The hydrophilic and hydrophobic surfactants are believed to function as absorption enhancers, and the hydrophilic surfactant additionally assists the functionality of other absorption enhancing hydrophilic or hydrophobic surfactants.

1. Surfactants

The absorption enhancing composition includes at least two surfactants, at least one of which is a hydrophilic surfactant. Preferably, the composition includes at least one hydrophilic surfactant and at least one hydrophobic surfactant. As is well known in the art, the terms "hydrophilic" and "hydrophobic" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and hydrophobicity of non-ionic amphiphilic compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences*, 79(1), 87–88 (1990)). Likewise, for certain polypropylene oxide containing block copolymers (PLURONIC® surfactants, BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

The choice of specific hydrophobic and hydrophilic surfactants should be made keeping in mind the particular hydrophilic therapeutic agent to be used in the composition, and the range of polarity appropriate for the chosen hydrophilic therapeutic agent, as discussed in more detail below. With these general principles in mind, a very broad range of surfactants is suitable for use in the present invention. Such surfactants can be grouped into the following general chemical classes detailed in the Tables herein. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value thax, in the judgment of the present inventors, is more reliable. It should be emphasized that the invention is not limited to the surfactants in the Tables, which show representative, but not exclusive, lists of available surfactants.

1.1. Polyethoxylated Fatty Acids

Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are especially useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 1.

TABLE 1

PEG-Fatty Acid Monoester Surfactants

| COMPOUND | COMMERCIAL PRODUCT (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400–1000 monostearate | Cithrol MS series (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200 ML (Stepan), LIPOPEG 2L (LIPO Chem.) | 9.3 |
| PEG-4 oleate | Mapeg ® 200 MO (PPG), Kessco ® PEG 200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG 300 ML (Stepan) | 11.4 |
| PEG-7 laurate | Lauridac 7 (Condea) | 13 |
| PEG-6 stearate | Kessco ® PEG 300 MS (Stepan) | 9.7 |
| PEG-8 laurate | Mapeg ® 400 ML (PPG), LIPOPEG 4DL (Lipo Chem.) | 13 |
| PEG-8 oleate | Mapeg ® 400 MO (PPG), Emulgante A8 (Condea); Kessco PEG 400 MO (Stepan) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor 59 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600 ML (Stepan) | 15 |
| PEG-12 oleate | Kessco ® PEG 600 MO (Stepan) | 14 |
| PEG-12 ricinoleate | (CAS #9004-97-1) | >10 |
| PEG-12 stearate | Mapeg ® 600 MS (PPG), Kessco ® PEG 600 MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

1.2 PEG-Fatty Acid Diesters

Polyethylene glycol (PEG) fatty acid diesters are also suitable for use as surfactants in the compositions of the present invention. Among the surfactants in Table 2, preferred hydrophilic surfactants include PEG-20 dilaurate, PEG-20 dioleate, PEG-20 distearate, PEG-32 dilaurate and PEG-32 dioleate. Representative PEG-fatty acid diesters are shown in Table 2.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 |
| PEG-4 dioleate | Mapeg ® 200 DO (PPG), | 6 |
| PEG-4 distearate | Kessco ® 200 DS (Stepan | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO (Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

1.3 PEG-Fatty Acid Mono- and Di-ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 3.

TABLE 3

PEG-Fatty Acid Mono- and Diester Mixtures

| COMPOUND | COMMERCIAL PRODUCT (Supplier) | HLB |
|---|---|---|
| PEG 4-150 mono, dilaurate | Kessco ® PEG 200–6000 mono, dilaurate (Stepan) | |
| PEG 4-150 mono, dioleate | Kessco ® PEG 200–6000 mono, dioleate (Stepan) | |
| PEG 4-150 mono, distearate | Kessco ® 200–6000 mono, distearate (Stepan) | |

1.4 Polyethylene Glycol Glycerol Fatty Acid Esters

Suitable PEG glycerol fatty acid esters are shown in Table 4. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 15 |
| PEG-20 glyceryl oleate | Tagat ® O (Goldschmidt) | >10 |
| PEG-30 glyceryl oleate | Tagat ® O2 (Goldschmidt) | >10 |

1.5. Alcohol-Oil Transesterification Products

A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, maltol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred hydrophobic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol M40), and PEG-20 almond glycerides (Crovol A40). The latter two surfactants are reported to have HLB values of 10, which is generally considered to be the approximate border line between hydrophilic and hydrophobic surfactants. For purposes of the present invention, these two surfactants are considered to be hydrophobic. Representative surfactants of this class suitable for use in the present invention are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants.

1.6. Polyglycerized Fatty Acids

Polyglycerol esters of fatty acids are also suitable surfactants for the present invention. Among the polyglyceryl fatty acid esters, preferred hydrophobic surfactants include polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Polyglyceryl polyricinoleates (Polymuls) are also preferred hydrophilic and hydrophobic surfactants. Examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3GO (ABITEC), Drewpol 3-1-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1-S (Nikko) | 5–6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G2O (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol ® 10G4O (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-101 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3–20 |

1.7. Propylene Glycol Fatty Acid Esters

Esters of propylene glycol and fatty acids are suitable surfactants for use in the present invention. In this surfactant class, preferred hydrophobic surfactants include propylene glycol monolaurate (Lauroglycol FCC), propylene glycol ricinoleate (Propymuls), propylene glycol monooleate (Myverol P-O6), propylene glycol dicaprylate/dicaprate (Captex® 200), and propylene glycol dioctanoate (Captex® 800). Examples of surfactants of this class are given in Table 7.

Table 7 includes both mono- and diesters of propylene glycol, and both may be used in one embodiment of the pharmaceutical systems of the present invention. In another embodiment, the absorption enhancing composition is free of both triglycerides and propylene glycol diesters.

1.8. Mixtures of Propylene Glycol Esters—Glycerol Esters

In general, mixtures of surfactants are also suitable for use in the present invention. In particular, mixtures of propylene glycol fatty acid esters and glycerol fatty acid esters are

TABLE 7

Propylene Glycol Fatty Acid Esters

| COMPOUND | COMMERCIAL PRODUCT (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-O6 (Eastman) | <10 |
| Propylene glycol dicaprylate/dicaprate | Captex ® 200 (ABITEC), Miglyol ® 840 (Hüls), Neobee ® M-20 (Stepan) | >6 |
| Propylene glycol dioctanoate | Captex ® 800 (ABITEC) | >6 |
| Propylene glycol caprylate/caprate | LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 | suitable and are commercially available. One preferred mixture is composed of the oleic acid esters of propylene glycol and glycerol (Arlacel 186). Examples of these surfactants are shown in Table 8.

TABLE 8

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3–4 |
| Stearic | ATMOS 150 | 3–4 |

1.9. Mono- and Diglycerides

A particularly important class of surfactants is the class of mono- and diglycerides. These surfactants are generally hydrophobic. Preferred hydrophobic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul® MCM), caprylic acid mono/diglycerides (Imwitor® 988), and mono- and diacetylated monoglycerides (Myvacet® 9–45). Examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECEOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18-92, Myverol 18-06 (Eastman) | 3–4 |
| Glyceryl ricinoleate | Softigen ® 701 (Hüls), HODAG GMR-D (Calgene), ALDO ® MR (Lonza) | 6 |
| Glyceryl monolaurate | ALDO ® MLD (Lonza), Rodag GML (Calgene) | 6.8 |
| Glycerol monopalmitate | Emalex GMS-P (Nihon) | 4 |
| Glycerol monostearate | Capmul ® GMS (ABITEC), Myvaplex (Eastman), IMWITOR ® 191 (Hüls), CUTINA GMS, Aldo ® MS (Lonza), Nikkol MGS series (Nikko) | 5–9 |
| Glyceryl mono-,dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Imwitor ® 312 (Hüls), Monomuls ® 90-45 (Grünau GmbH), Aldo ® MLD (Lonza) | 4 |
| Glyceryl citrate/lactate/oleate/linoleate | Imwitor ® 375 (Hüls) | <10 |
| Glyceryl caprylate | Imwitor ® 308 (Hüls), Capmul ® MCMC8 (ABITEC) | 5–6 |
| Glyceryl caprylate/caprate | Capmul ® MCM (ABITEC) | 5–6 |
| Caprylic acid mono, diglycerides | Imwitor ® 988 (Hüls) | 5–6 |
| Caprylic/capric glycerides | Imwitor ® 742 (Hüls) | <10 |
| Mono-and diacetylated monoglycerides | Myvacet ® 9-45, Myvacet ® 9-40, Myvacet ® 9-08 (Eastman), Lamegin ® (Grünau) | 3.8–4 |
| Glyceryl monostearate | Aldo ® MS, Arlacel 129 (ICI), LIPO GMS (Lipo Chem.), Imwitor ® 191 (Hüls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |

TABLE 9-continued

Mono- and Diglyceride Surfactants

| COMPOUND | COMMERCIAL PRODUCT (Supplier) | HLB |
|---|---|---|
| Glycerol esters of fatty acids | GELUCIRE 39/01 (Gattefosse), GELUCIRE 43/01 (Gattefosse) | 1 |
|  | GELUCIRE 37/06 (Gattefosse) | 6 |
| Dipalmitolein (C16:1) | (Larodan) | <10 |
| 1,2 and 1,3-diolein (C18:1) | (Larodan) | <10 |
| Dielaidin (C18:1) | (Larodan) | <10 |
| Dilinolein (C18:2) | (Larodan) | <10 |

1.10 Sterol and Sterol Derivatives

Sterols and derivatives of sterols are suitable surfactants for use in the present invention. These surfactants can be hydrophilic or hydrophobic. Preferred derivatives include the polyethylene glycol derivatives. A preferred hydrophobic surfactant in this class is cholesterol. A preferred hydrophilic surfactant in this class is PEG-24 cholesterol ether (Solulan C-24). Examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, lanosterol |  | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

1.11. Polyethylene Glycol Sorbitan Fatty Acid Esters

A variety of PEG-sorbitan fatty acid esters are available and are suitable for use as surfactants in the present invention. In general, these surfactants are hydrophilic, although several hydrophobic surfactants of this class can be used. Among the PEG-sorbitan fatty acid esters, preferred hydrophilic surfactants include PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Rodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleaie | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

1.12. Polyethylene Glycol Alkyl Ethers

Ethers of polyethylene glycol and alkyl alcohols are suitable surfactants for use in the present invention. Preferred hydrophobic ethers include PEG-3 oleyl ether (Volpo 3) and PEG-4 lauryl ether (Brij 30). Examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

1.13. Sugar Esters

Esters of sugars are suitable surfactants for use in the present invention. Preferred hydrophilic surfactants in this class include sucrose monopalmitate and sucrose monolaurate. Examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

1.14. Polyethylene Glycol Alkyl Phenols

Several hydrophilic PEG-alkyl phenol surfactants are available, and are suitable for use in the present invention. Examples of these surfactants are shown in Table 14.

wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

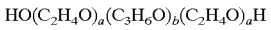

where "a" and "b" denote the number of polyoxyethylene and polyoxypropylene units, respectively.

Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

1.15. Polyoxyethylene-Polyoxypropylene Block Copolymers

The POE-POP block copolymers are a unique class of polymeric surfactants. The unique structure of the surfactants, with hydrophilic POE and hydrophobic POP moieties in well-defined ratios and positions, provides a Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in HO(C$_2$H$_4$O)$_a$(C$_3$H$_6$O)$_b$(C$_2$H$_4$O)$_3$H | | HLB |
|---|---|---|---|
| Poloxamer 105 | a = 1 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

1.16. Sorbitan Fatty Acid Esters

Sorbitan esters of fatty acids are suitable surfactants for use in the present invention. Among these esters, preferred hydrophobic surfactants include sorbitan monolaurate (Arlacel 20), sorbitan monopalmitate (Span-40), sorbitan monooleate (Span-80), sorbitan monostearate, and sorbitan tristearate. Examples of these surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

1.17. Lower Alcohol Fatty Acid Esters

Esters of lower alcohols (C$_2$ to C$_4$) and fatty acids (C$_8$ to C$_{18}$) are suitable surfactants for use in the present invention. Among these esters, preferred hydrophobic surfactants include ethyl oleate (Crodamol EO), isopropyl myristate (Crodamol IPM), and isopropyl palmitate (Crodamol IPP). Examples of these surfactants are shown in Table 17.

TABLE 17

Lower Alcohol Fatty Acid Ester Surfactants

| COMPOUND | COMMERCIAL PRODUCT (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

1.18. Ionic Surfactants

Ionic surfactants, including cationic, anionic and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown in Table 18. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
|---|---|
| FATTY ACID SALTS | >10 |
| Sodium caproate | |
| Sodium caprylate | |

TABLE 18-continued

Ionic Surfactants

| COMPOUND | HLB |
|---|---|
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |
| Sodium lithocholate | |
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

1.19 Ionizable Surfactants

Ionizable surfactants, when present in their un-ionized (neutral, non-salt) form, are hydrophobic surfactants suitable for use in the compositions and methods of the present invention, and in their ionized form, are hydrophilic surfactants suitable for use in the present invention. Particular examples of such surfactants include free fatty acids, particularly $C_6$–$C_{22}$ fatty acids, and bile acids. More specifically, suitable unionized ionizable surfactants include the free fatty acid and bile acid forms of any of the fatty acid salts and bile salts shown in Table 18. Preferred ionizable surfactants include fatty acids and their corresponding salts, such as caprylic acid/sodium caprylate, oleic acid/sodium oleate, capric acid/sodium caprate; ricinoleic acid/sodium ricinoleate, linoleic acid/sodium linoleate, and lauric acid/sodium laurate; trihydroxy bile acids and their salts, such as cholic acid (natural), glycocholic acid and taurocholic acid; dihydroxy bile acids and their salts, such as deoxycholic acid (natural), glycodeoxycholic acid, taurodeoxycholic acid, chenodeoxycholic acid (natural), glycochenodeoxycholic acid, taurochenodeoxycholic acid, ursodeoxycholic acid, tauroursodeoxycholic acid, and glycoursodeoxycholic acid; monohydroxy bile acids and their salts, such as lithocholic acid (natural); sulfated bile salt derivatives; sarchocholate; fusidic acid and its derivatives; phospholipids, such as phosphatidyl choline, phosphatidyl ethanolamine, phosphatidyl serine, PD inisitol, lysolecithin, and palmitoyl lysophosphatidyl choline; carnitines, such as palmitoyl carnitine, lauroyl carnitine and myristoyl carnitine; cyclodextrins, including alpha, beta and gamma cyclodextrins; and modified cyclodextrins, such as hydroxy propyl and sulfobutyl ether.

1.20 Preferred Surfactants and Surfactant Combinations

Among the above-listed surfactants, several combinations are preferred. In all of the preferred combinations, the absorption enhancing composition includes at least one hydrophilic surfactant. Preferred non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters: polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; and mixtures thereof.

More preferably, the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture.

Also preferred are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol is preferably glycerol, ethylene glycol, polyethylene glycol, sorbitol, propylene glycol, pentaerythritol, or a saccharide.

Several particularly preferred absorption enhancing compositions are those which include as a non-ionic hydrophilic surfactant PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG- 100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, or a poloxamer.

Among these preferred surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, and hydrophilic poloxamers.

The hydrophilic surfactant can also be, or include as a component, an ionic surfactant, i.e., the ionized form of an ionizable surfactant. Preferred ionic surfactants include the ionized form of alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-,diacetylated tartaric acid esters of mono-, diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

More preferable ionized ionizable surfactants include the ionized form of bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-, diacetylated tartaric acid esters of mono-,diglycerides, succinylated monoglycerides; citric acid esters of mono-, diglycerides; carnitines; and mixtures thereof.

More specifically, preferred ionized ionizable surfactants are the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Particularly preferred ionized ionizable surfactants are the ionized forms of lecithin, lysolecithin, phosphatidylcholine, phosphatidylethanolamine, phosphatidylglycerol, lysophosphatidylcholine, PEG-phosphatidylethanolamine, lactylie esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono/diacetylated tartaric acid esters of mono/diglycerides, citric acid esters of mono/ diglycerides, taurocholate, caprylate, caprate, oleate, lauryl sulfate, docusate, and salts and mixtures thereof.

The absorption enhancing compositions include at least two surfactants, at least one of which is hydrophilic. In one embodiment, the present invention includes at two surfactants that are hydrophilic, and preferred hydrophilic surfactants are listed above. In another embodiment, the composition includes at least one hydrophilic surfactant and at least one hydrophobic surfactant.

In this embodiment, the hydrophobic surfactant can be an unionized ionizable surfactant. Preferably, the unionized ionizable surfactant is the unionized form of a surfactant selected from the group consisting of bile acids and analogues and derivatives thereof; lecithins, lysolecithin, phospholipids, lysophospholipids and derivatives thereof; carnitine fatty acid esters; alkylsulfates; fatty acids; acyl lactylates; mono-,diacetylated tartaric acid esters of mono-, diglycerides; succinylated monoglycerides; citric acid esters of mono-,diglycerides; and mixtures thereof.

More preferably, the un-ionized ionizable surfactant is the un-ionized form of a surfactant selected from the group consisting of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholic acid, taurocholic acid, glycocholic acid, deoxycholic acid, taurodeoxycholic acid, chenodeoxycholic acid, lycodeoxycholic acid, glycochenodeoxycholic acid, taurochenodeoxycholic acid, ursodeoxycholic acid, lithocholic acid, tauroursodeoxycholic acid, glycoursodeoxycholic acid, cholylsarcosine, N-methyl taurocholic acid, caproic acid, caprylic acid, capric acid, lauric acid, myristic acid, palmitic acid, oleic acid, ricinoleic acid, linoleic acid, linolenic acid, stearic acid, lauryl sulfate, tetraacetyl sulfate, lauroyl carnitine, palmitoyl carnitine, myristoyl carnitine, and mixtures thereof.

Still more preferably, the un-ionized ionizable surfactant is the un-ionized form of a surfactant selected from the group consisting of lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholic acid, taurocholic acid, glycocholic acid, deoxycholic acid, chenodeoxycholic acid, lithocholic acid, ursodeoxycholic acid, taurodeoxycholic acid, glycodeoxycholic acid, cholylsarcosine, caproic acid, caprylic acid, capric acid, lauric acid, oleic acid, lauryl sulfate, lauroyl carnitine, palmitoyl carnitine, myristoyl carnitine, and mixtures thereof.

Most preferably, the un-ionized ionizable surfactant is the un-ionized form of a surfactant selected from the group consisting of lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, chenodeoxycholic acid, lithocholic acid, ursodeoxycholic acid, taurocholic acid, caprylic acid, capric acid, oleic acid, lauryl sulfate, docusate, lauroyl carnitine, palmitoyl carnitine, myristoyl carnitine, and mixtures thereof.

The hydrophobic surfactants can also be alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; and the un-ionized (neutral) forms of ionizable surfactants.

As with the hydrophilic surfactants, hydrophobic surfactants can be reaction mixtures of polyols and fatty acids, glycerides, vegetable oils, hydrogenated vegetable oils, and sterols.

Preferably, the hydrophobic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols.

More preferred are lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are preferably mono- or diglycerides, or mixtures of mono- and diglycerides, where the fatty acid moiety is a $C_6$ to $C_{22}$ fatty acid.

Also preferred are hydrophobic surfactants which are the reaction mixture of polyols and fatty acids, glycerides, vegetable oils, hydrogenated vegetable oils, and sterols. Preferred polyols are polyethylene glycol, sorbitol, propylene glycol, and pentaerythritol.

Specifically preferred hydrophobic surfactants include myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{20}$ fatty acid; monoglycerides of $C_6$ to $C_{20}$ fatty acids; acetylated monoglycerides of $C_6$ to $C_{20}$ fatty acids; diglycerides of $C_6$ to $C_{20}$ fatty acids; lactic acid derivatives of monoglycerides; lactic acid derivatives of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; and poloxamers.

Among the specifically preferred hydrophobic surfactants, most preferred are oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; and poloxamers.

2. Therapeutic Agents

The hydrophilic therapeutic agents suitable for use in the pharmaceutical systems and methods of the present invention are not particularly limited, as the absorption enhancing compositions are surprisingly capable of delivering a wide variety of hydrophilic therapeutic agents. Suitable hydrophilic therapeutic agents include hydrophilic drugs (i.e., conventional non-peptidic drugs), hydrophilic macromolecules such as cytokines, peptidomimetics, peptides, proteins, toxoids, sera, antibodies, vaccines, nucleosides, nucleotides and genetic material, and other hydrophilic compounds, such as nucleic acids. The aqueous solubility of the hydrophilic therapeutic agent should be greater than about 1 mg/mL.

The hydrophilic therapeutic agent can be solubilized or suspended in a preconcentrate (before dilution with an aqueous diluent), added to the preconcentrate prior to dilution, added to the diluted preconcentrate, or added to an aqueous diluent prior to mixing with the preconcentrate. The hydrophilic therapeutic agent can also be co-administered as part of an independent dosage form, for therapeutic effect. Optionally, the hydrophilic therapeutic agent can be present in a first, solubilized amount, and a second, non-solubilized (suspended) amount. Such hydrophilic therapeutic agents can be any agents having therapeutic or other value when administered to an animal, particularly to a mammal, such as drugs, nutrients, cosmetics (cosmeceuticals), and diagnostic agents. It should be understood that while the invention is described with particular reference to its value for oral dosage forms, the invention is not so limited. Thus, hydrophilic drugs, nutrients, cosmetics and diagnostic agents which derive their therapeutic or other value from, for example, transmembrane (transport across a membrane barrier of therapeutic significance), nasal, buccal, rectal, vaginal or pulmonary administration, are still considered to be suitable for use in the present invention.

Specific non-limiting examples of therapeutic agents that can be used in the pharmaceutical compositions of the present invention include analgesics and anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents and immunosuppressants, anti-protozoal agents, anti-thyroid agents, anti-tussives, anxiolytic, sedatives, hypnotics and neuroleptics, β-Blockers, cardiac inotropic agents, corticosteroids, diuretics, anti-parkinsonian agents, gastrointestinal agents, histamine H,-receptor antagonists, keratolytics, lipid regulating agents, muscle relaxants, anti-anginal agents, nutritional agents, analgesics, sex hormones, stimulants, cytokines, peptidomimetics, peptides, proteins, toxoids, sera, antibodies, vaccines, nucleosides, nucleotides and genetic material, and nucleic acids. Amphiphilic therapeutic agents are also included, provided they have a water solubility of greater than about 1 mg/mL.

In one embodiment, the hydrophilic therapeutic agent is a nutritional agent.

In another embodiment, the hydrophilic therapeutic agent is a cosmeceutical agent.

In another embodiment, the hydrophilic therapeutic agent is a diagnostic agent.

Although the invention is not limited thereby, examples of hydrophilic therapeutic agents suitable for use in the compositions and methods of the present invention include the following preferred compounds, as well as their pharmaceutically acceptable salts, isomers, esters, ethers and other derivatives:

acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones- recombinant human; growth hormone- bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metroprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin;

stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopessin derivatives; vecoronium bromide; vinbiastin; vincristine; vinorelbine; vitamin B12; warfarin sodium; yellow fever vaccine; zalcitabine; zanamavir; zolandtronate; and zidovudine.

Among the listed hydrophilic therapeutic agents, more preferred therapeutic agents are:

acarbose; acyclovir; atracurium besylate; alendronate; anglucerase; amantadine hydrochloride; amphotericin B; antihemophilic factor (human); antihemophilic factor (porcine); antihemophilic factor (recombinant; azithromycin; calcitonin human; calcitonin salmon; capecitabine; cefazolin sodium; cefonicid sodium; cefoperazone; cefoxitin sodium; ceftizoxime; ceftriaxone; cefuroxime axetil; cephalexin; chrionic gonadotropin; cidofovir; cladribine; clindamycin and clindamycin derivatives; cortocotropin; cosyntropin; cromalyn sodium; cytarabine; daltaperin sodium; danaproid; desmopressin; didanosine; dirithromycin; editronate disodium; enoxaprin sodium; epoetin alpha; factor IX; famiciclovir; fludarabine; foscaret sodium; ganciclovir; granulocyte colony stimulating factor; granulocyte-macrophage stimulating factor; growth hormones- recombinant human; growth hormone-Bovine; gentamycin; glucagon; gonadotropin releasing hormone and synthetic analogs thereof; GnRH; gonadorelin; hemophilus B conjugate vaccine; Hepatitis A virus vaccine inactivated; Hepatitis B virus vaccine inactivated; heparin sodium; indinavir sulfate; vinfluenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; lamivudine; leucovorin calcium; leuprolide acetate; lincomycin and lincomycin derivatives; metformin hydrochloride; nedocromil sodium; neostigmine bromide; neostigmine methyl sulfate; neutontin; octreotide acetate; olpadronate; pamidronate disodium; pancuronium bromide; pentamindine isethionate; pentagastrin; physostigmine salicylate; poliovirus vaccine live (OPV); pyridostigmine bromide; residronate; ribavarin; rimantadine hydrochloride; rotavirus vaccine; salmetrol xinafoate; somatostatin; spectinomycin; stavudine; streptokinase; ticarcillin; tiludronate; tissue type plasminogen activator; TNFR:Fc; TNK-tPA; trimetrexate gluconate; trospectinomycin; tumor necrosis factor; typhoid vaccine live; urokinase; vancomycin; valaciclovir; vasopressin and vasopressin derivatives; vinblastin; vincristine; vinorelbine; warfarin sodium; zalcitabine; zanamavir; and zidovudine.

The most preferred hydrophilic therapeutic agents are:

acarbose; alendronate; amantadine hydrochloride; azithromycin; calcitonin human; calcitonin salmon; ceftriaxone; cefuroxime axetil; chrionic gonadotropin; cromalyn sodium; daltaperin sodium; danaproid; desmopressin; didanosine; editronate disodium; enoxaprin sodium; epoetin alpha; factor IX; famiciclovir; foscarnet sodium; ganciclovir; granulocyte colony stimulating factor; granulocyte-macrophage stimulating factor; growth hormones-recombinant human; growth hormone- Bovine; glucagon; gonadotropin releasing hormone and synthetic analogs thereof; GnRH; gonadorelin; heparin sodium; indinavir sulfate; influenza virus vaccine; interleukin-2; interleukin-3; insulin-human; insulin lispro; insulin procine interferon alpha; interferon beta; leuprolide acetate; metformin hydrochloride; nedocromil sodium; neostigmine bromide; neostigmine methyl sulfate; neutontin; octreotide acetate; olpadronate; pamidronate disodium; residronate; rimantadine hydrochloride; salmetrol xinafoate; somatostatin; stavudine; ticarcillin; tiludronate; tissue type plasminogen activator; TNFR:Fc; TNK-tPA; tumor necrosis factor; typhoid vaccine live; vancomycin; valaciclovir; vasopressin and vasopressin derivatives; zalcitabine; zanamavir and zidovudine.

Of course, salts, metabolic precursors, derivatives and mixtures of therapeutic agents may also be used where desired.

3. Solubilizers

If desired, the pharmaceutical compositions of the present invention can optionally include additional compounds to enhance the solubility of the therapeutic agent or the triglyceride in the composition. Examples of such compounds, referred to as "solubilizers", include:

alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives;

ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

amides, such as 2-pyrrolidone, 2-piperidone, $\epsilon$-caprolactam, N-alkylpyrrolidone, N-hydroxyalkylpyrrolidone, N-alkylpiperidone, N-alkylcaprolactam, dimethylacetamide, and polyvinylpyrrolidone;

esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof;

and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water.

Mixtures of solubilizers are also within the scope of the invention. Except as indicated, these compounds are readily available from standard commercial sources.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included in compositions of the present invention is not particularly limited. Of course, when such compositions are ultimately administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of therapeutic agent, with excess solubilizer removed prior to providing the composition to a patient using conventional techniques, such as distillation or evaporation. Thus, if present, the solubilizer can be in a concentration of 50%, 100%, 200%, or up to about 400% by weight, based on the weight of the carrier. If desired, very small amounts of solubilizers may also be used, such as 25%, 10%, 5%, 1% or even less. Typically, the solubilizer will be present in an amount of about 1% to about 100%, more typically about 5% to about 25% by weight or about 10% to about 25% by weight.

4. Concentrations

The components of the absorption enhancing compositions of the present invention are present in amounts such that upon dilution with an aqueous diluent, the carrier forms an aqueous dispersion having a small particle size. The hydrophilic and optional hydrophobic surfactants should be present in amounts sufficient to improve the absorption of the hydrophilic therapeutic agent. It is surprisingly found that relatively large amounts of the surfactants can be used while still maintaining a small particle size upon dilution.

Without wishing to be bound by theory, it is believed that the absorption enhancers present in the compositions are able to enhance absorption by one or more of the following factors: effective presentation of an absorption enhancer to the site of enhancement; modulation of facilitated/active transport; transcellular permeability enhancement through favorable membrane perturbations; inhibition of efflux related transporters; inhibition of lumenal or cellular enzymatic inactivation; paracellular transport enhancement through loosening of tight junctions; induction of specific transporters to facilitate transport; altered biological binding characteristics; reduced degradation of the hydrophilic therapeutic agent; induction of transient water channels; and/or increased partitioning of the hydrophilic therapeutic agent by association with the absorption enhancer. The functionality is believed to be due to a combination of small particle size, appropriate absorption enhancers in amounts chosen to provide small particle size upon dilution, and non-dependence upon lipolysis by avoiding the use of triglycerides. Preferably, diesters of propylene glycol are also avoided.

The presence of at least two surfactants, at least one of which is hydrophilic, is believed to be particularly advantageous to provide better presentation of the absorption enhancing components at the absorption site. For example, the presence of each surfactant is believed to assist the absorption enhancement functionality of the other surfactants by reducing the size of the particles containing the absorption enhancing surfactant to minimize aqueous boundary layer control, and/or by solubilizing water-immicible absorption enhancing surfactants to increase the thermodynamic activity of the surfactant at the absorption site.

A preferred method of assessing the appropriate component concentrations is to quantitatively measure the size of the particles of which the dispersion is composed. These measurements can be performed on commercially available particle size analyzers, such as, for example, a Nicomp particle size analyzer available from Particle Size Systems, Inc., of Santa Barbara, Calif. Using this measure, aqueous dispersions according to the present invention have average particle sizes much smaller than the wavelength of visible light, whereas dispersions containing relative amounts of the components outside the appropriate range have more complex particle size distributions, with much greater average particle sizes. It is desirable that the average particle size be less than about 200 nm, preferably less than about 100, more preferably less than about 50 nm, still more preferably less than about 30 nm, and most preferably less than about 20 nm. It is also preferred that the particle size distribution be mono-modal. These particle sizes can be measured at dilution amounts of 10 to 250-fold or more, preferably about 100 to about 250-fold, as is typical of the dilution expected in the gastrointestinal tract.

In a preferred embodiment, the components of the absorption enhancing compositions are present in amounts such that the aqueous dispersion formed upon dilution with an aqueous medium has a small particle size and is also substantially optically clear. The composition in the preconcentrate form, i.e., before dilution with an aqueous diluent, need not be clear, as it is the clarity upon dilution with an aqueous diluent that is preferred. The dilution can be in vitro or in vivo, and optical clarity should be assessed at dilutions of about 10 to 250-fold or more, preferably about 100 to 250-fold, as is encountered in the gastrointestinal environment. It should be appreciated that where the desired dosage form includes an amount of the hydrophilic therapeutic agent that is suspended, but not solubilized, in the composition, the appropriate concentrations of the other components are determined by the optical clarity of the diluted composition without the suspended therapeutic agent.

In this preferred embodiment, the relative amounts of the components are readily determined by observing the properties of the resultant dispersion; i.e., when the relative amounts are within the preferred range, the resultant aqueous dispersion is optically clear. When the relative amounts are outside the preferred range, the resulting dispersion is visibly "cloudy", resembling a conventional emulsion or multiple-phase system. The optical clarity of the aqueous dispersion can be measured using standard quantitative techniques for turbidity assessment. One convenient procedure to measure turbidity is to measure the amount of light of a given wavelength transmitted by the solution, using, for example, a UV-visible spectrophotometer. Using this measure, optical clarity corresponds to high transmittance, since cloudier solutions will scatter more of the incident radiation, resulting in lower transmittance measurements. If this procedure is used, care should be taken to insure that the composition itself does not absorb light of the chosen wavelength, as any true absorbance necessarily reduces the amount of transmitted light and falsely increases the quantitative turbidity value. In the absence of chromophores at the chosen wavelength, suitable dispersions at a dilution of 100× should have an apparent absorbance of less than about 0.3, preferably less than about 0.2, and more preferably less than about 0.1.

Other methods of characterizing optical clarity known in the art may also be used, and any or all of the available methods may be used to ensure that the resulting aqueous dispersions possess the preferred optical clarity.

In one embodiment, the hydrophilic therapeutic agent is formulated in the dosage form of the absorption enhancing composition, and is present in any amount up to the maximum amount that can be solubilized in the composition. In another embodiment, the hydrophilic therapeutic agent is present in the dosage form of the absorption enhancing composition in a first amount which is solubilized, and a second amount that remains unsolubilized but dispersed. This may be desirable when, for example, a larger dose of the hydrophilic therapeutic agent is desired. Of course, in this embodiment, the optical clarity or particle size of the resultant aqueous dispersion is determined before the second non-solubilized amount of the hydrophilic therapeutic agent is added. In another embodiment, the hydrophilic therapeutic agent is present in a dosage form separate from the dosage form of the absorption enhancing composition, and the amount of hydrophilic therapeutic agent is any convenient amount that can be formulated in the separate dosage form, such as a therapeutically effective amount. This separate dosage form of the hydrophilic therapeutic agent can be a dosage form of the present invention, or any conventional dosage form, preferably triglyceride free, such as a commercial dosage form.

Other considerations well known to those skilled in the art will further inform the choice of specific proportions of the components. These considerations include the degree of bioacceptablity of the compounds, and the desired dosage of hydrophilic therapeutic agent to be provided.

Keeping the considerations discussed above in mind, it is important that the composition include sufficient amounts of the absorption enhancing components to provide a therapeutically meaningful increase in the rate and/or extent of bioabsorption. Thus, in general the total amount of absorption enhancing components forming the carrier should be at least about 10% by weight, preferably at least about 20%, based on the total weight of the preconcentrate composition. As shown in the examples herein, the total amount of the absorption enhancing components can be far greater than 20%, and these compositions are also within the scope of the present invention.

It is preferred that when the absorption enhancing composition includes at least two surfactants selected from the group consisting of sodium lauryl sulfate, oleic acid, linoleic acid, monoolein, lecithin, lysolecithin, deoxycholate, taurodeoxycholate, glycochenodeoxycholate, polyoxyethylene X-lauryl ether, where X is from 9 to 20, sodium tauro-24,25-dihydrofusidate, polyoxyethylene ether, polyoxyethylene sorbitan esters, p-t-octylphenoxypolyoxyethylene, N-lauryl-β-D-maltopyranoside, 1-dodecylazacycloheptane-2-azone, and phospholipids, each surfactant is present in an amount of greater than 10% by weight, based on the total weight of the pharmaceutical system.

Alternatively, appropriate coating can be applied to the dosage form to enable sufficient concentration/amount of the absorption enhancing surfactant/therapeutic agent/inhibitor at the site of absorption.

5. Stability 5.1 Enzyme Inhibitors

When the hydrophilic therapeutic agent is subject to enzymatic degradation, the compositions can include an enzyme inhibiting agent as an absorption enhancing agent. Enzyme inhibiting agents are shown for example, in Bernskop-Schnurch, A., "The use of inhibitory agents to overcome enzymatic barrier to perorally administered therapeutic peptides and proteins", *J. Controlled Release* 52, 1–16 (1998), the disclosure of which is incorporated herein by reference.

Generally, inhibitory agents can be divided into the following classes:

Inhibitors that are not based on amino acids, such as P-aminobenzamidine, FK-448, camostat mesylate, sodium glycocholate;

Amino acids and modified amino acids, such as aminoboronic acid derivatives and n-acetylcysteine;

Peptides and modified peptides, such as bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, and amastatin;

Polypeptide protease inhibitors, such as aprotinin (bovine pancreatic trypsin inhibitor), Bowman-Birk inhibitor and soybean trypsin inhibitor, chicken egg white trypsin inhibitor, chicken ovoinhibitor, and human pancreatic trypsin inhibitor;

Complexing agents, such as EDTA, EGTA, 1,10-phenanthroline and hydroxychinoline; and Mucoadhesive polymers and polymer-inhibitor conjugates, such as polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bowman-Birk inhibitor.

The choice and levels of the enzyme inhibitor are based on toxicity, specificity of the proteases and the potency of the inhibition. Enteric coated compositions of the present invention protect hydrophilic therapeutic peptides or proteins in a restricted area of drug liberation and absorption, and reduce or even exclude extensive dilution effects. The inhibitor can be suspended or solubilized in the composition preconcentrate, or added to the aqueous diluent or as a beverage.

Without wishing to be bound by theory, it is believed that an inhibitor can function solely or in combination as:

a competitive inhibitor, by binding at the substrate binding site of the enzyme, thereby preventing the access to the substrate; examples of inhibitors believed to operate by this mechanism are antipain, elastatinal and the Bowman Birk inhibitor;

a non-competitive inhibitor which can be simultaneously bound to the enzyme site along with the substrate, as their binding sites are not identical; and/or a complexing agent due to loss in enzymatic activity caused by deprivation of essential metal ions out of the enzyme structure.

5.2 Water-Free Preconcentrates

In a particular embodiment, the preconcentrate absorption enhancing composition—ie., the composition before dispersion in an aqueous medium—is free of water. Water-free compositions are preferred to increase the physical and/or chemical stability of the composition or of individual components thereof, allowing for longer storage. In addition, water-free compositions offer advantages in processing, such as, for example, ease in encapsulation.

6. Other Additives

Other additives conventionally used in pharmaceutical compositions can be included, and these additives are well known in the art. Such additives include detackifiers, antifoaming agents, buffering agents, antioxidants, preservatives, chelating agents, viscomodulators, tonicifiers, flavorants, colorants odorants, opacifiers, suspending agents, binders, fillers, plasticizers, lubricants, and mixtures thereof. The amounts of such additives can be readily determined by one skilled in the art, according to the particular properties desired.

An acid or a base may be added to the composition to facilitate processing, or to prevent degradation of the hydrophilic therapeutic agent. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide. diisopropylethylamine, ethanolamine, ethyleuediamine, triethanolamine, triethylamine, triisopropanolamine, and the like. Also suitable are bases which are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Although a wide variety of absorption enhancing components, solubilizers and additives can be used in the pharmaceutical systems of the present invention, in one embodiment, it is preferred that the composition be water-free in the preconcentrate form. In another embodiment, it is preferred that the composition be free of propylene glycol diesters. In another embodiment, it is preferred that the composition be free of cholesterol. Of course, combinations of these preferred embodiments are also within the scope of the invention, so that the composition may, for example, be free of several or all of water, propylene glycol diesters and cholesterol.

7. Dosage Forms

The pharmaceutical compositions of the present invention can be formulated as a preconcentrate in a liquid, semi-solid, or solid form, or as an aqueous or organic diluted preconcentrate. In the diluted form, the diluent can be water, an aqueous solution, a buffer, an organic solvent, a beverage, a juice, or mixtures thereof. If desired, the diluent can include components soluble therein, such as a hydrophilic therapeutic agent, an enzyme inhibitor, solubilizers, additives, and the like.

The compositions can be processed according to conventional processes known to those skilled in the art, such as lyophilization, encapsulation compression, melting, extrusion, balling, drying, chilling, molding, spraying, spray congealing, coating, comminution, mixing, homogenization, sonication, cryopelletization, spheronization, and granulation, to produce the desired dosage form.

The dosage form is not particularly limited. Thus, compositions of the present invention can be formulated as pills, capsules, caplets, tablets, granules, pellets, beads or powders. Granules, pellets, beads and powders can, of course, be further processed to form pills, capsules, caplets or tablets.

The dosage form can be designed for immediate release, controlled release, extended release, delayed release or targeted delayed release. The definitions of these terms are known to those skilled in the art. Furthermore, the dosage form release profile can be effected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Such dosage forms can further be coated with, for example, a seal coating, an enteric coating, an extended release coating, or a targeted delayed release coating.

The term "extended release coating" as used herein means a coating designed to effect the delivery of a hydrophilic therapeutic agent, an enzyme inhibitor, or the carrier, over an extended period of time. Preferably, the extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery of a hydrophilic therapeutic agent, an absorption enhancing carrier or an enzyme inhibitor to both the small and large intestines, to only the small intestine, or to only the large intestine, depending upon the choice of coating materials and/or coating thickness.

Dosage forms of the compositions of the present invention can also be formulated as enteric coated delayed release oral dosage forms, i.e., as an oral dosage form of a pharmaceutical composition as described herein which utilizes an enteric coating to effect release of a hydrophilic therapeutic agent, enzyme inhibitor and/or absorption enhancing carrier in the lower gastrointestinal tract. The enteric coated dosage form may be a compressed or molded or extruded tablet/mold (coated or uncoated) containing granules, pellets, beads or particles of the hydrophilic therapeutic agent, enzyme inhibitor and/or absorption enhancing carrier, which are themselves coated or uncoated. The enteric coated oral dosage form may also be a capsule (coated or uncoated) containing pellets, beads or granules of the hydrophilic therapeutic agent, enzyme inhibitor and/or absorption enhancing carrier which are themselves coated or uncoated.

The term "enteric coating" as used herein relates to a mixture of pharmaceutically acceptable excipients which is applied to, combined with, mixed with or otherwise added to the hydrophilic therapeutic agent, enzyme inhibitor and/or absorption enhancing carrier. The coating may be applied to a compressed or molded or extruded tablet, a gelatin capsule, and/or pellets, beads, granules or particles of the hydrophilic therapeutic agent, enzyme inhibitor and/or absorption enhancing carrier. The coating mar be applied through an aqueous dispersion or after dissolving in appropriate solvent. Additional additives and their levels, and selection of a primary coating material or materials will depend on the following properties:

1. resistance to dissolution and disintegration in the stomach;

2. impermeability to gastric fluids and drug/carrier/ enzyme while in the stomach;

3. ability to dissolve or disintegrate rapidly at the target intestine site;

4. physical and chemical stability during storage;

5. non-toxicity;

6. easy application as a coating (substrate friendly); and, 7. economical practicality.

The term "delayed release" as used herein refers to the delivery of the hydrophilic therapeutic agent, an enzyme inhibitor, and/or the absorption enhancing carrier, which is effected by formulating the composition so that the release can be accomplished at some generally predictable location in the lower intestinal tract more distal to that which would have been accomplished if there had been no delayed release alterations. The preferred method for delay of release is coating. Coating prevents exposure of the hydrophilic therapeutic agent, enzyme inhibitor and/or absorption enhancing carrier to the epithelial and mucosal tissue of the buccal cavity, pharynx, esophagus, and stomach, and to the enzymes associated with these tissues. This helps to protect the hydrophilic therapeutic agent, enzyme inhibitor and/or absorption enhancing carrier and the tissues from any adverse event prior to the delivery at the desired site of absorption. Furthermore, coated compositions of the present invention allow balancing enhancement effectiveness, active protection, and safety liability through coating controlled dilution of the hydrophilic therapeutic agent, enzyme inhibitor and/or absorption enhancing carrier upon administration through delayed release or sustained release. Multiple enteric coatings targeted to release hydrophilic therapeutic agent, enzyme inhibitor and/or absorption enhancing carrier at various regions in the lower gastrointestinal tract would enable even more effective and sustained improved delivery throughout the lower gastrointestinal tract.

Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery of the hydrophilic therapeutic agent, enzyme inhibitor and/or absorption enhancing carrier to the lower gastrointestinal tract. The coating chosen should be compatible with the hydrophilic therapeutic agent and the other selected components. The preferred polymers for use in the present invention are anionic carboxylic polymers. The more preferred polymers and compatible mixtures thereof, and some of their properties, include, but are not limited to:

Shellac, also called purified lac, a refined product obtained from the resinous secretion of an insect. This coating dissolves in media of pH>7.

Acrylic polymers (preferred). The performance of acrylic polymers (primarily their solubility in biological fluids) can vary based on the degree and type of substitution. Examples of suitable acrylic polymers include methacrylic acid copolymers and ammonio methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for extended release. The Eudragit series E dissolve in the stomach. The Eudragit series L, L-30D and S are insoluble in stomach and dissolve in the intestine.

Cellulose Derivatives (also preferred). Examples of suitable cellulose derivatives are:

ethyl cellulose;

reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 $\mu$m. Other components in Aquateric can include pluronics, Tweens, and acetylated monoglycerides;

cellulose acetate trimellitate (Eastman);

methylcellulose (Pharmacoat, Methocel);

hydroxypropyl methyl cellulose phthalate (HPMCP). The performance can vary based on the degree and type of substitution. HP-50, HP-55, HP-55S HP-55F grades are suitable;

hydroxypropyl methyl cellulose succinate (HPMCS; AQOAT (Shin Etsu)).

The performance can vary based on the degree and type of substitution. Suitable grades include AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids; and Cotteric (by Colorcon).

Combinations of the above materials can also be used.

The coating can, and usually does, contain a plasticizer and possibly other coating excipients such as colorants, talc, and/or magnesium stearate, which are well known in the art. Suitable plasticizers include: triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10–25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the lower intestinal tract is reached.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

A particularly suitable methacrylic copolymer is Eudragit L.RTM, particularly L-30D.RTM and Eudragit 100–55. RTM, manufactured by Rohm Pharma, Germany. In Eudragit L-30 D.RTM, the ratio of free carboxyl groups to ester groups is approximately 1:1. Further, the copolymer is known to be insoluble in gastrointestinal fluids having pH below 5.5, generally 1.5–5.5, i.e., the pH generally present in the fluid of the upper gastrointestinal tract, but readily soluble or partially soluble at pH above 5.5, i.e., the pH generally present in the fluid of lower gastrointestinal tract.

Another methacrylic acid polymer which is suitable for use in coating the oral dosage forms and/or the granules, particles, pellets or beads of absorption enhancing carrier and/or hydrophilic therapeutic agent which can be employed in the compositions and methods described herein, either alone or in combination with other coatings, is Eudragit S.RTM, manufactured by Rohm Pharma, Germany. Eudragit S.RTM. differs from Eudragit L-30-D.RTM only insofar as the ratio of free carboxyl groups to ester groups is approximately 1:2. Eudragit S.RTM is insoluble at pH below 5.5, but unlike Eudragit L-30-D.RTM, is poorly soluble in gastrointestinal fluids having pH of 5.5–7.0, such as is present in the small intestine media. This copolymer is soluble at pH 7.0 and above, i.e., the pH generally found in the colon. Eudragit S.RTM can be used alone as a coating to provide delivery of the hydrophilic therapeutic agent and/or the absorption enhancing carrier beginning at the large intestine via a delayed release mechanism. In addition, Eudragit S.RTM, being poorly soluble in intestinal fluids below pH 7, can be used in combination with Eudragit L-30-D.RTM, soluble in intestinal fluids above pH 5.5, in order to effect a delayed release composition which can be formulated to deliver the hydrophilic therapeutic agent and/or absorption enhancing carrier to various segments of the intestinal tract. The more Eudragit L-30 D.RTM used the more proximal realease and delivery begins, and the more Eudragit S.RTM used, the more distal release and delivery begins Both Eudragit L-30-D-RTM and Eudragit S.RTM can be substituted with other pharmaceutically acceptable polymers with similar pH solubility characteristics.

Preferred materials include shellac, acrylic polymers, cellulosic derivatives, polyvinyl acetate phthalate, and mixtures thereof. More preferred materials include Eudragit series E, L, S, RL, RS, NE, L.RTM, L300.RTM, S.RTM, 100-55RTM, cellulose acetate phthalate, Aquateric, cellulose acetate trimellitate, ethyl cellulose, hydroxypropyl methyl cellulose phthalate, hydroxypropyl methyl cellulose succinate, poly vinyl acetate phthalate, and Cotteric. Most preferred materials include Eudragit series L.RTM, L300.RTM, S.RTM, L100-55RTM, cellulose acetate phthalate, Aquateric, ethyl cellulose, hydroxypropyl methyl cellulose phthalate, hydroxypropyl methyl cellulose succinate, poly vinyl acetate phthalate, and Cotteric.

Extended release and targeted delayed release coatings for dosage forms of the compositions of the present invention are described more completely in U.S. Pat. Nos. 5,622,721 and 5,686,105, the disclosures of which are incorporated herein by reference in their entirety.

Although formulations specifically suited to oral administration are presently preferred, the compositions of the present invention can also be formulated for topical, transdermal, buccal, nasal, ocular, pulmonary, vaginal, rectal, transmucosal or parenteral administration, as well as for oral administration. Thus, the dosage form can be a solution, suspension, emulsion, cream, ointment, lotion, suppository, spray, aerosol, paste, gel, drops, douche, ovule, wafer, troche, cachet, syrup, elixer, or other dosage form, as desired. If formulated as a suspension, the composition can further be processed in capsule form.

When formulated as a sprayable solution or dispersion, a dosage form of a multiparticulate carrier coated onto a substrate with the pharmaceutical compositions described herein can be used. The substrate can be a granule, a particle, a pellet or a bead, for example, and formed of a therapeutic agent or a pharmaceutically acceptable material. The multiparticulate carrier can be enteric coated with a pharmaceutically acceptable material, such as the targeted delayed enteric coatings and extended release coatings of U.S. Pat. Nos. 5,622,721 and 5,686,105, described above. The multiparticulate carrier, coated or uncoated, can further be processed by encapsulation, and the resultant capsule can also be coated, if desired.

Other additives may be included, such as are well-known in the art, to impart the desired consistency and other properties to the formulation.

8. Specific Embodiments

In all of the embodiments described herein, the components of the absorption enhancing carrier are present in amounts such that upon mixing with an aqueous diluent, either in vitro or in vivo, the carrier forms an aqueous dispersion having a small average particle size. In a preferred embodiment, the dispersion is also substantially optically clear. In these preferred embodiments, the optical clarity or particle size in an aqueous dispersion defines the preferred relative concentrations of the components as described above, but does not restrict the dosage form of the compositions to an aqueous dispersion, nor does it limit the compositions of the invention to optically clear dosage forms. Thus, the preferred concentrations of the components are determined by the particle size and/or optical clarity of a dispersion formed by the composition preconcentrate and an aqueous diluent in a dilution of about 10 to about 250-fold, as a preliminary matter. Once the appropriate concentrations are determined, the pharmaceutical compositions can be formulated as described in the preceding section, without regard to the optical clarity of the ultimate formulation in these preferred embodiments.

In one particular embodiment, the present invention provides a triglyceride-free pharmaceutical system including an absorption enhancing composition including at least two surfactants, at least one of which is hydrophilic. The surfactants are present in amounts such that the carrier forms an aqueous dispersion having a small average particle size. In one preferred aspect of this embodiment, the average particle size is less than about 200 nm upon mixing with an aqueous diluent. In another preferred aspect of this embodiment, the aqueous dispersion is substantially optically clear. Preferably, the composition includes a mixture of hydrophilic and hydrophobic surfactants.

The pharmaceutical system also includes a hydrophilic therapeutic agent. The hydrophilic therapeutic agent can be solubilized, suspended, or partially solubilized and suspended, in the dosage form of the absorption enhancing composition. Alternatively, the hydrophilic therapeutic agent can be provided in a separate dosage form, so that in use, the dosage form of the absorption-enhancing composition and the dosage form of the hydrophilic therapeutic agent are co-administered. In the latter aspect, the pharmaceutical system can make use of any dosage form of a hydrophilic therapeutic agent, such as commercially available dosage forms. The pharmaceutical system is particularly advantageous, since the absorption enhancing pharmaceutical composition improves the functionality of even conventionally formulated hydrophilic therapeutic agents. Preferably, the dosage form of the absorption enhancing pharmaceutical composition, with or without a hydrophilic therapeutic agent, is an orally administrable dosage form. If the hydrophilic therapeutic agent is provided in a separate dosage form, it is preferred that the dosage form of the hydrophilic therapeutic agent also be an orally administrable dosage form.

In another aspect, the present invention provides a method of improving the bioabsorption of a hydrophilic therapeutic agent administered to a patient, such as an animal, preferably a mammal, and more preferably a human. The method includes the steps of providing a dosage form of an absorption enhancing composition, providing a hydrophilic therapeutic agent, and administering the dosage form of the absorption enhancing composition and the hydrophilic therapeutic agent to the patient. The dosage form of the absorption enhancing composition can be any of the dosage forms described above. Similarly, the hydrophilic therapeutic agent can be provided solubilized, suspended, or partially solubilized and suspended, in the dosage form of the absorption enhancing composition, or can be provided in a separate dosage form. It is surprisingly found that by administering a hydrophilic therapeutic agent contained within, or co-administered with, a dosage form of an absorption enhancing composition of the present invention, the rate and/or extent, or the consistency in the rate and/or extent of bioabsorption of the hydrophilic therapeutic agent is unexpectedly enhanced. Thus, in one aspect the method increases the rate and/or extent of bioabsorption. In another aspect, the method increases the consistency of the rate and/or extent of bioabsorption. In this latter aspect, the rate and/or extent of bioabsorption can be greater than or less than the rate that would be seen using conventional methods.

In other embodiments, the absorption enhancing compositions in the pharmaceutical systems and methods of the present invention can be free of water in the preconcentrate form, free of propylene glycol diesters, and/or free of cholesterol. All of the compositions, however, are substantially free of triglycerides.

9. Preparation of Pharmaceutical Compositions

The pharmaceutical compositions of the present invention can be prepared by conventional methods well known to those skilled in the art. Of course, the specific method of preparation will depend upon the ultimate dosage form. For dosage forms substantially free of water, i.e., when the composition is provided in a pre-concentrate form for later dispersion in vitro or in vivo in an aqueous system, the composition is prepared by simple mixing of the components to form a pre-concentrate. The mixing process can be aided by gentle heating, if desired. For compositions in the form of an aqueous dispersion, the pre-concentrate form is prepared, then the appropriate amount of an aqueous diluent is added. Upon gentle mixing, an aqueous dispersion is formed. If any water-soluble enzyme inhibitors or additives are included, these may be added first as part of the pre-concentrate, or added later to the aqueous dispersion, as desired. The dosage forms of the absorption enhancing compositions can be prepared with or without a hydrophilic therapeutic agent, and a hydrophilic therapeutic agent may also be provided in the diluent, if desired, or in a separate dosage form.

As previously noted, in another embodiment, the present invention includes a multi-phase dispersion containing a hydrophilic therapeutic agent. In this embodiment, a dosage form includes a hydrophilic therapeutic agent and an absorption enhancing composition which forms an aqueous dispersion upon mixing with an aqueous diluent, and an additional amount of non-solubilized hydrophilic therapeutic agent. Thus, the term "multi-phase" as used herein to describe these compositions of the present invention means a composition which when mixed with an aqueous diluent forms an aqueous phase and a particulate dispersion phase. The composition components are as described above, and can include any of the surfactants, therapeutic agents, solubilizers and additives previously described. An additional amount of hydrophilic therapeutic agent is included in the composition. This additional amount is not solubilized in the composition, and upon mixing with an aqueous system is present as a separate dispersion phase. The additional amount is optionally a milled, micronized, or precipitated form. Thus, upon dilution, the composition contains two phases: an aqueous dispersion phase containing a first, solubilized amount of the hydrophilic therapeutic agent, and a second, non-solubilized amount of the hydrophilic therapeutic agent dispersed therein.

One skilled in the art will appreciate that a hydrophilic therapeutic agent may have a greater solubility in the pre-concentrate composition than in the aqueous dispersion, so that meta-stable, supersaturated solutions having apparent optical clarity but containing a hydrophilic therapeutic agent in an amount in excess of its solubility in the aqueous dispersion can be formed. Such super-saturated solutions, whether characterized as aqueous dispersions (as initially formed) or as multi-phase solutions (as would be expected if the meta-stable state breaks down), are also within the scope of the present invention.

The multi-phase formulation can be prepared by the methods described above. A pre-concentrate is prepared by simple mixing of the components, with the aid of gentle heating, if desired. It is convenient to consider the hydrophilic therapeutic agent as divided into two portions, a first solubilizable portion which will be solubilized and contained within the clear aqueous dispersion upon dilution, and a second non-solubilizable portion which will remain non-solubilized. When the ultimate dosage form is non-aqueous, the first and second portions of the hydrophilic therapeutic agent are both included in the pre-concentrate mixture. When the ultimate dosage form is aqueous, the composition can be prepared in the same manner, and upon dilution in an aqueous system, the composition will form the two phases as described above, with the second non-solubilizable portion of the hydrophilic therapeutic agent dispersed or suspended in the aqueous system, and the first solubilizable portion of the hydrophilic therapeutic agent solubilized in the composition. Alternatively, when the ultimate dosage form is aqueous, the pre-concentrate can be prepared including only the first, solubilizable portion of the hydrophilic therapeutic agent. This pre-concentrate can then be diluted in an aqueous system to form an aqueous dispersion, to which is then added the second, non-solubilizable portion of the hydrophilic therapeutic agent to form a multi-phase aqueous composition.

B. Characteristics of the Pharmaceutical Compositions and Methods

The dispersions formed upon dilution of the pharmaceutical compositions of the present invention are believed to have some or all of the following characteristics:

Rapid formation: upon dilution with an aqueous diluent, the composition forms an aqueous dispersion of small particle size very rapidly; i.e., the dispersion appears to form instantaneously.

Optical clarity: in a preferred embodiment, the dispersions are essentially optically clear to the naked eye, and show no readily observable signs of heterogeneity, such as turbidity or cloudiness. More quantitatively, dispersions of the pharmaceutical compositions of the present invention have absorbances (400 nm) of less than about 0.3, and generally less than about 0.1, at 100× dilution in this preferred embodiment. In the multi-phase embodiment of the compositions described herein, it should be appreciated that the optical clarity of the aqueous phase will be obscured by the dispersed particulate non-solubilized hydrophilic therapeutic agent.

Small Particle Size: dispersions of the pharmaceutical compositions of the present invention contain particles of very small size. Preferably, the average size is less than about 200 nm, more preferably less than about 100 nm, still more preferably less than about 50 nm and most preferably less than about 20 nm. The small particle size promotes efficient transport of the absorption enhancing components to the absorption site.

Robustness to dilution: the dispersions are surprisingly stable to dilution in aqueous solution. The absorption enhancing composition remains solubilized for at least the period of time relevant for absorption.

The unique pharmaceutical compositions and methods of the present invention present a number of significant and unexpected advantages, including:

Efficient transport: The particle sizes in the aqueous dispersions of the present invention are much smaller than the larger particles characteristic of vesicular, emulsion or microemulsion phases. This reduced particle size enables more efficient transport through the intestinal aqueous boundary layer, and through the absorptive brush border membrane. More efficient transport to absorptive sites leads to improved and more consistent absorption of therapeutic agents. Moreover, the present invention allows absorption enhancing components to be delivered to the absorption site along with the hydrophilic therapeutic agent, to further enhance absorption.

No dependence on lipolysis: The lack of triglycerides provides pharmaceutical compositions that are not dependent upon lipolysis, and upon the many poorly characterized factors which affect the rate and extent of lipolysis, for effective presentation of a therapeutic agent to an absorptive site. Such factors include the presence of composition components which may inhibit lipolysis; patient conditions which limit production of lipase, such as pancreatic lipase secretory diseases; and dependence of lipolysis on stomach pH, endogenous calcium concentration, and presence of co-lipase or other digestion enzymes. The lack of lipolysis dependence further provides transport which is less prone to suffer from any lag time between administration and absorption caused by the lipolysis process, enabling a more rapid onset of therapeutic action and better bioperformance characteristics. In addition, pharmaceutical compositions of the present invention can make use of hydrophilic surfactants which might otherwise be avoided or limited due to their potential lipolysis inhibiting effects.

Non-denendence on bile and meal fat contents: Due to the higher solubilization potential over bile salt micelles, the present compositions are less dependent on endogenous bile and bile related patient disease states, and meal fat contents. These advantages overcome meal-dependent absorption problems caused by poor patient compliance with meal-dosage restrictions.

Faster dissolution and release: Due to the robustness of compositions of the present invention to dilution, the components of the absorption enhancing composition remain solubilized and thus do not suffer problems of precipitation or agglomeration in the time frame relevant for absorption. In addition, the therapeutic agent is presented in small particle carriers, and is not limited in dilution rate by entrapment in emulsion carriers.

Consistent performance: Aqueous dispersions of the present invention are thermodynamically stable for the time period relevant for absorption, and can be more predictably reproduced, thereby limiting variability in bioavailability—a particularly important advantage for therapeutic agents with a narrow therapeutic index.

Less prone to gastric emptying delays: Unlike conventional triglyceride-containing formulations, the present compositions are less prone to gastric emptying delays, resulting in faster absorption. Further, the particles in dispersions of the present invention are less prone to unwanted retention in the gastrointestinal tract.

Better targeted absorption: The compositions of the present invention can be targeted to specific absorption sites through targeted enteric coating or extended release coating, thus minimizing dilution effects and optimizing activity of the hydrophilic therapeutic agent.

These and other advantages of the present invention, as well as aspects of preferred embodiments, are illustrated more fully in the Examples which follow.

EXAMPLES

Example 1

Preparation of Compositions

A simple pre-concentrate is prepared as follows. Predetermined weighed amounts of the components are stirred together to form a homogeneous mixture. For combinations that are poorly miscible, the mixture can be gently heated to aid in formation of the homogeneous mixture. If the composition is to include a hydrophilic therapeutic agent, the chosen hydrophilic therapeutic agent in a predetermined amount can be added and stirred until solubilized. Optionally, solubilizers or additives are included by simple mixing.

To form an aqueous dispersion of the pre-concentrate, a predetermined amount of an aqueous medium such as purified water, buffer solution, or aqueous simulated physiological solution, is added to the pre-concentrate, and the resultant mixture is stirred to form an aqueous dispersion. Of course, when the dosage form is an aqueous dispersion, any of the components that are readily water-soluble, including the hydrophilic therapeutic agent, can be provided in the diluent solution.

Examples 2–3

Membrane Transport and In Situ Absorption Studies

Compositions of the present invention were tested by two different methods, to demonstrate the improved delivery of hydrophilic therapeutic agents incorporated within or co-administered with compositions including an absorption enhancing carrier. In one set of studies, the relative permeability of membranes to hydrophilic therapeutic agents was compared with and without the presence of an absorption enhancing carrier ("Membrane Transport Study"). In a second set of studies, the relative absorption of a hydrophilic therapeutic agent in rat mesenteric veins was compared with and without the presence of an absorption enhancing carrier ("Relative Absorption Study").

For Examples 2 and 3, the following compositions were used, as described in the following sections. For each sample composition, absorbance measurements were made at 400 nm, using a UV-Visible spectrophotometer, at a dilution of 25× with distilled water. In addition, particle size measurements were made using a particle size analyzer, and the volume-weighted average particle sizes are shown along with sample characteristics in Table 19. The standard deviation of the particle size distribution is shown in parentheses next to the average particle size.

TABLE 19

Sample Compositions and Characterizations

| Sample No. | Components | Amounts (g) | Absorbance | Size (nm) |
|---|---|---|---|---|
| 1 | Cremophor RH40 | 0.50 | 0.016 | 14.1 (2.5) |
|   | Labrasol | 0.20 | | |
|   | Capmul MCM | 0.30 | | |
| 2 | Tween 20 | 0.67 | 0.039 | 12.3 (2.1) |
|   | Lauroglycol | 0.16 | | |
|   | Glycofurol | 0.17 | | |
| 3 | Cremophor RH40 | 0.30 | 0.004 | 9.0 (1.6) |
|   | Arlacel 186 | 0.20 | | |
|   | Sodium taurocholate | 0.18 | | |
|   | Propylene glycol | 0.32 | | |
| 4 | Cremophor RH40 | 0.54 | 0.167 | 17.6 (3.8) |
|   | Span 80 | 0.26 | | |
|   | PEG 400 | 0.20 | | |
| 5 | Cremophor RH40 | 0.06 | 2.497 | 2610 (564) |
|   | Arlacel 186 | 0.62 | | |
|   | Propylene glycol | 0.32 | | |
| 6 | Cremophor RH40 | 0.49 | −0.010 | 13.8 (2.3) |
|   | Propylene glycol | 0.51 | | |

Note that Sample Nos. 5 and 6 are control samples. Sample No. 5 was observed to form a cloudy emulsion upon mixing with an aqueous diluent, and fails to show a small particle size. Sample No. 6 contains only one surfactant.

Example 2

Membrane Transport Studies

Experimental

The membrane transport studies of model hydrophobic therapeutic agents were carried out across the CACO-2 monolayers. The Caco-2 cell line, originating from a human carcinoma, was obtained from the American Type Culture collection and was grown to form confluent monolayers as described elsewhere (I. J. Hidalgo, T. J. Raub, and R. T. Borchardt, *Gastroenterology* 96:736–749 (1989)). All cells used in this study were between 50 and 60 passage number. The cells were measured for confluency by measurement of TEER (trans epithelial electrical resistance) values. Monolayers exhibiting similar TEER values consistent with "non leakiness" were used to study and compare transport characteristics of model actives in plain buffer and in presence of diluted compositions of the present invention.

In duplicate, all transport experiments were performed for 2 hrs at 37° C. in pH 7.35 HBSS containing 25 mM glucose and 10 mM Hepes buffer. Prior to the experiments, the culture medium of Transwell grown Caco-2 cell monolayers was replaced with transport medium equilibrated at 37° C., and the cell monolayer was subsequently equilibrated before undertaking transport studies.

Two hydrophilic therapeutic agents, foscarnet and PEG-4000, were tested. Foscarnet sodium is a low molecular weight (192 g/mol) hydrophilic antiviral that inhibits viral DNA polymerase and reverse transcriptase. It is very soluble in water, shows $pK_a$s of 0.5, 3.4 and 7.3, and has a log of octanol/water partition coefficient of −2.0 (at pH 7.4). Apical to basal transport of the model hydrophilic actives foscarnet sodium and polyethylene glycol 4000 (PEG-4000) was studied by spiking the transport medium, a plain buffer or a 100× buffer dilution of the composition under investigation, with one micro curie of radio-labeled active on the apical side. Basolateral appearance of the active was monitored by taking appropriate samples and assaying for radioactivity. Permeability coefficients (P) were calculated using the following equation:

$$P=(dQ/dt)/(AC_0)$$

where P is the permeability coefficient, dQ/dt is the flux across the monolayer (DPM/min), A is the surface area of the membrane, and $C_0$ is the initial concentration of the active.

Results:

Table 20 shows the apical to basal membrane transport of a conventional hydrophilic active, foscarnet sodium in Sample Nos. 1–3, and a model macromolecular hydrophilic active, PEG-4000, in Sample No. 4, compared to a plain buffer solution

TABLE 20

Permeability for a Conventional Hydrophilic Active

| Sample No. | Active | $(P_{sample}^a/P_{buffer}^b) \times 100$ |
|---|---|---|
| 1 | foscarnet sodium | 1007 |
| 2 | foscarnet sodium | 195 |
| 3 | foscarnet sodium | 160 |
| 4 | PEG-4000 | 188 |

[a] permeability in the presence of 100× diluted composition
[b] permeability in the presence of buffer only Example 3

Relative Absorption Study

Experimental:

The sample preconcentrate solutions were diluted with standard hypotonic PBS pH 7.4 buffer. Two hydrophilic therapeutic agents were studied: a conventional hydrophilic active, acyclovir, and the model macromolecular active, PEG-4000.

For the acyclovir compositions, the compositions after dilution were spiked with 0.1 mM cold acyclovir, then 0.5 microliter of tritiated acyclovir (specific activity 18.9 Ci/mmol) was added to the diluted composition. The osmotic pressure was adjusted with sodium chloride as needed. The resulting aqueous isotonic dispersions were perfused through rat intestinal segments to assess absorption enhancement in a procedure described below. Appearance of the active was monitored in the mesenteric blood along with disappearance on the lumenal side.

Surprisingly, appreciable levels of the conventional hydrophilic active were noted in the blood compared to control perfusion studies conducted with plain buffer and with the control samples 5 (milky emulsion-forming preconcentrate) and 6 (plain one surfactant concentrate), showing that the compositions of the present invention increased absorption characteristics of very hydrophilic actives.

For the model macromolecular active, radio labeled PEG-4000 was added to a diluted (50×) pre-concentrate, and the resulting clear aqueous isotonic dispersion was perfused through a rat intestinal segment to assess absorption enhancement in a procedure described below. Appearance of the active was monitored in the mesenteric blood along with disappearance on the lumenal side. Surprisingly, as with the acyclovir, appreciable levels of hydrophilic active were noted in the blood compared to control perfusion studies conducted with plain buffer, showing the unexpected result that the compositions of the present invention increased permeability characteristics of very hydrophilic macromolecular actives.

Procedure:

Young adult (275–300 g) male Sprague Dawley rats were used. The procedures were consistent with those reported by Winne et al., "In vivo studies of mucosal-serosal transfer in rat jejunum", *Naunyn-Schmeideberg's Arch. Pharmacol.*, 329, 70 (1985).

Jugular vein cannulation: the animal was anesthetized using 2% halothane in 98% oxygen via a halothane vaporizer (Vapomatic, A.M. Bickford, Inc., N.Y.). An opening in the jugular vein was made with a 21 gauge needle and a jugular cannula consisting of a 4 cm segment of silastic tubing connected to polyethylene tubing was inserted in the jugular vein and secured with cyanoacrylate glue. For the donor rat, approximately 20 mL of blood was freshly collected in the presence of heparin (1,000 units) and the collected blood was infused at a rate of 0.2 mL/min through the jugular vein in the experimental rat to replenish blood sampling.

Intestine cannulation: after the animal was anesthetized, its body temperature was maintained at 37° C. using a heating pad. A vertical midline incision of approximately 3 cm was made through the skin to expose the small intestine. Approximately 6–10 cm segment of ileum was located. Using electro-cautery, a small incision was made at the ends of the segment and the lumenal contents were flushed with saline maintained at 37° C. Two 1.5 cm notched pieces of Teflon tubing were inserted into the intestinal lumen at each incision and tightened using 4-0 silk. A warm isotonic buffer was passed through the intestine using a 50-mL syringe. These teflon cannula were used to perfuse the drug solution through the isolated intestinal segment using a syringe pump.

Mesenteric vein cannulation: the mesenteric vein draining blood from the resulting isolated mesenteric cascade venule was then cannulated using a 24 gauge IV catheter and secured in place using 4-0 silk sutures. The cannula was then connected to a polyethylene tubing 25 cm long where the blood was collected in a vial kept under the animal level. Blood samples were collected continuously over 60 to 90 min. The infusion of blood via the jugular vein was initiated to replenish blood loss.

Results:

I. Conventional Hydrophilic Active (acyclovir)

The experiment was performed twice for each of the test samples and control buffer compositions. For each formulation, the results of the two trials were averaged. The cumulative amount of radioactivity for the duration of the study as a fraction of total radioactivity exposed to the intestinal segment was monitored for each trial to assess absorption. The % relative absorption results for a conventional hydrophilic active (acyclovir) in presence of various diluted example compositions compared to a plain buffer are presented in Table 21. The relative absorption reported in Table 21 is 100 times the ratio of the fraction of the total amount administered in mesenteric blood when perfused with the 25× diluted compositions to the fraction of the total amount administered when perfused with the plain buffer, over the same time period.

TABLE 21

Relative Absorption of Acyclovir

| Sample No. | % Relative Absorption |
|---|---|
| 1 | 614 |
| 2 | 634 |
| 3 | 704 |
| Control Samples: | |
| 5 | 171 |
| 6 | 141 |

Surprisingly, appreciable bioenhancement was observed only for compositions that had at least one hydrophilic surfactant plus a second surfactant, and that formed very small dispersions upon dilution (Sample Nos. 1–3), showing that effective presentation of carrier at the absorption site is very critical. In contrast, compositions that contained the same surfactants but formed larger unstable emulsion upon dilution (Sample No. 5) due to poor choice of concentration, or contained only a single surfactant (Sample No. 6) resulted in only marginal bioenhancement over plain buffer.

II. Macromolecular Hydrophilic Active

The results for a macromolecular hydrophilic active is presented in Table 22. The experiment was performed twice for each composition. The relative absorption shown in the Table is for a 50× dilution

TABLE 22

Relative Absorption of a Macromolecular Active

| Sample No. | % Relative Absorption |
|---|---|
| 3 | 991 |

In comparison to negligible absorption of PEG 4000 in presence of plain buffer, the absorption of PEG 4000 in the presence of a composition of the present invention gave surprising high absorption. This demonstrates the improved absorption of macromolecules with compositions of the present invention.

Example 4

Absorption Enhancing Carriers

Typical surfactant ratios consistent with the invention that can be prepared are listed. Additives can be included as discussed herein, and the concentrations can be varied as desired to render the compositions easy to prepare, stable upon storage, bioacceptable and elegant, provided that the concentrations are such that the carrier forms an aqueous dispersion having a small particle size, upon dilution with an aqueous medium. Adequate enzyme inhibitor, bufferants, other additives and organic solubilizers can be included at pharmaceutically acceptable levels. Hydrophilic therapeutic agents can be added at levels convenient for therapeutic effect.

| A: Compositions Having At least Two Hydrophilic Surfactants | |
|---|---|
| Sodium taurocholate | 0.18 g |
| Cremophor RH 40 | 0.30 g |
| Sodium chenodeoxycholate | 0.30 g |
| Tween 80 | 0.50 g |
| Sodium Sarcocholate | 0.15 g |
| Crovol M-70 | 0.60 g |
| Sodium lithocholate | 0.30 g |
| Labrasol | 0.55 g |
| Sodiun glycocholate | 0.10 g |
| Tween 20 | 0.50 g |
| Sodium ursodeoxycholate | 0.30 |
| Incrocas-35 | 0.50 |
| Chenodeoxycholic acid | 0.25 g |
| Cremophor RH 40 | 0.50 g |
| Cremophor RH 40 | 0.60 g |
| Sodium caprate | 0.10 g |
| Cremophor RH 40 | 0.50 g |
| Palmitoyl carnitine | 0.20 g |
| Solulan C-24 | 0.60 g |
| Sodium chenodeoxycholate | 0.25 g |
| Taurocholate | 0.20 g |
| Egg or Soy lecithin | 0.09 g |

-continued

| | |
|---|---|
| Tween 20 | 0.30 g |
| Sodium taurocholate | 0.20 g |
| Tween 20 | 0.25 g |
| Egg lecithin | 0.15 g |
| Chenodeoxycholate | 0.18 g |
| $C_{18}$ lysolipid | 0.10 g |
| Chenodeoxycholate | 0.20 g |
| Oleic acid | 0.10 g |
| Labrasol | 0.20 g |
| Brij 35 | 0.75 g |

B: Compositions Having One Hydrophilic and One Hydrophobic Surfactant

| | |
|---|---|
| Cremophor EL-P | 0.83 g |
| Peceol | 0.17 g |
| Cremophor EL-P | 0.50 g |
| Propylene glycol monocaprate | 0.20 g |
| Cremophor EL-P | 0.50 g |
| Imwitor 375 | 0.20 g |
| Cremophor EL-P | 0.50 g |
| Nikkol MGM | 0.18 g |
| Cremophor RH 40 | 0.50 g |
| Arlacel 186 | 0.10 g |
| Cremophor RH 40 | 1.53 g |
| Arlacel 186 | 0.38 |
| HPB cyclodextrin | 0.18 g |
| Cremophor RH 40 | 0.55 g |
| Capmul MCM | 0.80 g |
| Cremophor RH 40 | 0.50 g |
| Crodamol (ethyl oleate) | 0.28 g |
| Cremophor RH 40 | 0.50 g |
| Labrafril | 0.40 g |
| Cremophor RH 40 | 0.22 g |
| Lauroglycol FCC | 0.20 g |
| Cremophor RH 40 | 0.60 g |
| Glyceryl monolaurate | 0.20 g |
| Cremophor RH-40 | 0.43 g |
| Myvacet 9-45 | 0.31 g |
| Cremophor RH-40 | 0.30 g |
| Peceol | 0.11 g |
| Cremophor RH40 | 0.50 g |
| Propyleneglycol monololeate | 0.20 g |
| Cremophor RH40 | 0.50 g |
| Softigen 701 | 0.10 g |
| Cremophor RH40 | 0.50 g |
| Sorbitan monocaprate | 0.25 g |
| Cremophor RH 60 | 0.54 g |
| Span 80 | 0.26 g |
| Cremophor RH 40 | 0.70 g |
| Volpo 3 | 0.30 g |
| Crodet O40 | 0.68 g |
| Plurol Oleique | 0.32 g |
| Crovol M-70 | 0.61 g |
| Crovol M-40 | 0.12 g |
| Crovol M-70 | 0.38 g |
| Labrafil | 0.60 g |
| Crovol M-70 | 0.65 g |
| Imwitor 988 | 0.15 g |
| Crovol M-70 | 0.60 g |
| Linoleic acid | 0.20 g |
| Emalex C-40 | 0.50 g |
| Gelucire 33/01 | 0.15 g |
| Glycerox L | 0.73 g |
| Myvacet 9-45 | 0.27 g |
| Incrocas 35 | 0.65 g |
| Arlacel 186 | 0.12 g |
| Incrocas 35 | 0.25 g |
| Gelucire 44/14 | 0.15 g |
| Incrocas 35 | 0.83 g |
| Imwitor 988 | 0.20 g |
| Incrocas 35 | 0.31 g |
| Labrafil | 0.11 g |
| Labrasol | 0.83 g |
| Lauroglycol | 0.17 g |
| Lauroyl carnitine | 0.15 g |
| Imwitor 312 | 0.15 g |
| Incrocas 35 | 0.50 g |
| Myvacet 9-45 | 0.38 g |
| Incrocas-35 | 0.50 g |

-continued

| | |
|---|---|
| Span-20 | 0.15 g |
| Incrocas 35 | 0.51 g |
| Imwitor 988 | 0.22 g |
| Kessco PEG 300DL | 0.35 g |
| Gelucire 50/15 | 0.50 g |
| Kessco PEG 1540DO | 0.65 g |
| Span 80 | 0.12 |
| Labrasol | 0.45 g |
| Span-20 | 0.25 g |
| Myrj 45 | 0.50 g |
| Sorbitan monocaprylate | 0.25 g |
| Myrj 52 | 0.50 g |
| Imwitor 308 | 0.20 g |
| Sucrose monolaurate | 0.50 g |
| Capmul MCM | 0.20 g |
| Nikkol Decaglyn 1-L | 0.55 g |
| Crovol M-40 | 0.33 g |
| Nikkol Decaglyn 1-O | 0.65 g |
| Capmul MCM | 0.25 g |
| Nikkol DHC | 0.67 g |
| Nikkol TMGO-5 | 0.17 g |
| Nikkol BPS-30 | 0.30 g |
| PEG-6 castor oil | 0.15 g |
| Tween 20 | 0.75 g |
| Drewpol 6-1-0 | 0.15 g |
| Tween 20 | 0.34 g |
| Lauroglycol FCC | 0.11 g |
| Tween 20 | 0.58 g |
| Plurol Oleique | 0.21 g |
| Tween 80 | 0.67 g |
| Lauroglycol | 0.17 g |
| Tagat O2 | 0.50 g |
| PGMG-03 | 0.05 g |
| Tagat L2 | 0.68 g |
| Brij 30 | 0.32 g |
| Poloxamer 188 | 0.85 g |
| Labrafil M2125CS | 0.15 g |
| Poloxamer 108 | 0.85 g |
| Capmul GMO-K | 0.15 g |
| Solulan C-24 | 0.58 g |
| Lauroglycol FCC | 0.21 g |

C: Two Hydrophilic Surfactants and One Hydrophobic Surfactant

| | |
|---|---|
| Cremophor EL | 0.30 g |
| Labrasol | 0.30 g |
| Capmul MCM | 0.40 g |
| Cremophor RH-40 | 0.25 g |
| Labrasol | 0.25 g |
| Capmul GMO-K | 0.11 g |
| Cremophor RH 40 | 0.30 g |
| Tween-20 | 0.20 g |
| Nikkol Decaglyn 3-O | 0.50 g |
| Cremophor EL-P | 0.45 g |
| Corvol M-40 | 0.25 g |
| Sodium Docusate | 0.15 g |
| Cremophor RH 40 | 0.65 g |
| Arlacel 186 | 0.15 g |
| Sodium dodecyl sulfate | 0.10 g |
| Cremophor RH 40 | 0.50 g |
| Peceol | 0.20 g |
| Sodium docusate | 0.20 g |
| Sodium Chenodeoxycholate | 0.30 g |
| Cremophor RH 40 | 0.40 g |
| Arlacel 186 | 0.30 g |
| Cremophor RH 40 | 0.41 g |
| Sodium taurocholate | 0.26 g |
| Arlacel 186 | 0.27 g |
| Cremophor RH 40 | 0.50 g |
| Softigen 767 | 0.22 g |
| Arlacel 186 | 0.15 g |
| Cremophor RH 40 | 0.40 g |
| Arlacel 186 | 0.40 g |
| Tween 20 | 0.20 g |
| Cremophor RH 40 | 0.35 g |
| Capmul MCM | 0.30 g |
| Sodium chenodeoxycholate | 0.30 g |
| Kessco PEG 1000MO | 0.30 g |
| Labrasol | 0.30 g |
| Span 20 | 0.40 g |

-continued

| | |
|---|---|
| Polaxamer 188 | 0.65 g |
| Peceol | 0.15 g |
| Sodium dodecyl sulfate | 0.10 g |
| Sodium taurocholate | 0.17 g |
| Tween 20 | 0.66 g |
| Arlacel 186 | 0.17 g |
| Sodium taurocholate | 0.17 g |
| Kessco PEG 1000MO | 0.66 g |
| Plurol Oleique | 0.17 g |
| Sodium taurocholate | 0.15 g |
| Tween 80 | 0.18 g |
| Arlacel 186 | 0.18 g |
| Taurochenodeoxycholate | 0.15 g |
| Tween 20 | 0.40 g |
| Arlacel 186 | 0.15 g |
| Chenodeoxycholic acid | 0.25 g |
| Incrocas-35 | 0.30 g |
| Span 20 | 0.20 g |
| Saurcocholate | 0.20 g |
| Cremophor RH 40 | 0.40 g |
| Arlacel 186 | 0.20 g |
| Lithocholate | 0.25 g |
| Incrocas-35 | 0.40 g |
| Myvacet 9-45 | 0.30 g |
| Tagat L2 | 0.45 g |
| Crovol A-40 | 0.25 g |
| Sodium docusate | 0.15 g |
| Tween-20 | 0.30 g |
| Arlacel 186 | 0.20 g |
| Sodium chenodeoxycholate | 0.25 g |
| Cremophor RH 40 | 0.40 g |
| Tween-20 | 0.25 g |
| Sodium caprate | 0.25 g |
| Cremophor RH40 | 0.40 g |
| Lauric acid | 0.20 g |
| Incrocas-35 | 0.30 g |
| D: One Hydrophilic and Two Hydrophobic Surfactants | |
| Cremophor RH 40 | 0.50 g |
| Labrafil M2125CS | 0.27 g |
| Crovol M-40 | 0.28 g |
| Cremophor RH 40 | 1.53 g |
| Arlacel 186 | 0.38 g |
| Peceol | 0.38 g |
| HPB beta cyclodextrin | 0.38 g |
| Cremophor RH 40 | 0.55 g |
| Labrafil M2125 CS | 0.34 g |
| Span 80 | 0.2 g |
| Cremophor RH 40 | 0.50 g |
| Labrafil M2125 Cs | 0.27 g |
| Crovol M-40 | 0.28 g |
| E: Two Hydrophilic and Two Hydrophobic Surfactants | |
| Polaxamer 108 | 0.45 g |
| Span 20 | 0.25 g |
| Sodium docusate | 0.15 g |
| Ethyl oleate | 0.15 g |
| Softigen 767 | 0.45 g |
| Imwitor 742 | 0.25 g |
| Sodium docusate | 0.15 g |
| Ethyl oleate | 0.15 g |

Example 5

Compositions with Hydrophilic Therapeutic Agent

Typical compositions having a hydrophilic therapeutic agent can have components and concentrations in the following exemplary, but not limiting ranges, in percent by weight unless otherwise indicated:

| | |
|---|---|
| absorption enhancing composition | 10–100% |
| enzyme Inhibitor (e.g., aprotinin) | 0–10% |

-continued

| | |
|---|---|
| solubilizer (e.g., propylene glycol) | 0–60% |
| bufferant | 0–50 mM |
| hydrophilic polymer (e.g., HPMC) | 0–20% w/w |
| other additives | 0–50% |

If formulated as an aqueous dosage form, a typical amount of water would be about 250 mL, or any other convenient amount.

Typical hydrophilic therapeutic agents and amounts in mg or IU/mL or G:

| | |
|---|---|
| alendronate Sodium | 5–50 mg |
| etidronate disodium | 200–400 mg |
| pamidronate disodium | 30–90 mg |
| aztreonam | 20–500 mg |
| valacylcovir | 250–1000 mg |
| gancyclovir | 250–500 mg |
| famcyclovir | 125–200 mg |
| pericyclovir | 125–1000 mg |
| pyridostigmine | 60 mg |
| cromalyn sodium | 0.1–2 mg |
| nedocromil sodium | 0.1–2 mg |
| metformin hydrochloride | 500–850 mg |
| acarbose | 50–100 mg |
| amphotericin B | 50–200 mg |
| octreotide acetate | 0.1 to 1 mg |
| cefoxitin sodium | 200–1000 mg |
| corticotropin: | 25–1000 IU |
| sodium heparin | 20–5000 IU |
| desmopressin acetate (DVAP) | 0.1–1 mg |
| vasopressin | 5–100 IU |
| salmon calcitonin | 500 IU |
| insulin | 140 IU |
| erythropoietin | 14,000 mg |
| porcine somatotropin | 50 mg |
| recombinant growth hormone | 30 IU |
| oligonucleotide | 1–500 mg |

Of course, the amounts listed are chosen to be therapeutically effective amounts, but the invention is not limited thereby.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A pharmaceutical system for enhanced absorption of a hydrophilic therapeutic agent, the system consisting essentially of:
    (a) a dosage form of an absorption enhancing composition, the composition comprising:
        (i) at least one hydrophilic surfactant selected from the group consisting of ionized ionizable surfactants, non-ionic hydrophilic surfactants having an HLB value greater than or equal to about 10, and combinations thereof, and
        (ii) at least one hydrophobic surfactant selected from the group consisting of hydrophobic (a) alcohols, polyoxyethylene alkylethers, bile acids, glycerol fatty acid monoesters, glycerol fatty acid diesters, acetylated glycerol fatty acid monoesters, acetylated glycerol fatty acid diesters, lower alcohol fatty acid monoesters, lower alcohol fatty acid diesters, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, un-ionized (b) fatty acids, carnitine fatty acid esters, alkylsulfates, acyl lactylates, mono-acetylated tartaric acid esters of mono- and diglycerides, diacetylated tartaric acid esters of mono- and diglycerides, succinylated monoglycerides, citric acid esters of mono- and diglycerides, and mixtures thereof, wherein the hydrophilic and hydrophobic surfactants are present in amounts such that upon mixing with an aqueous diluent at 100× dilution, the composition forms a clear aqueous dispersion having an absorbance of less than about 0.3 at 400 nm; and (b) a therapeutically effective amount of a hydrophilic therapeutic agent, wherein the pharmaceutical system is free of triglycerides.

2. The pharmaceutical system of claim 1, wherein the hydrophilic surfactant comprises at least one ionized ionizable surfactant.

3. The pharmaceutical system of claim 2, wherein the ionized ionizable surfactant is the ionized form of a surfactant selected from the group consisting of bile acids and salts, analogues, and derivatives thereof; carntine fatty acid ester salts; salts of alkylsulfates; salts of fatty acids; sodium docusate; acyl lactylates; mono-acetylated tartaric esters of mono- and diglycerides, diacetylated tartaric acid esters of mono- and diglycerides; succinylated monoglycerides; citric acid esters of mono- and diglycerides; and mixtures thereof.

4. The pharmaceutical system of claim 2, wherein the ionized ionizable surfactant is the ionized form of a surfactant selected from the group consisting of lactylic esters of fatty acids, stearoyl-2-lactylate, stearoyl lactylate, succinylated monoglycerides, mono-acetylated tartaric esters of mono- and diglycerides, diacetylated tartaric acid esters of mono- and diglycerides, citric acid esters of mono- and diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, lithocholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, tetraacetyl sulfate, docusate, lauroyl carnitine, palmitoyl carnitine, myristoyl carnitine, and salts and mixtures thereof.

5. The pharmaceutical system of claim 2, wherein the ionized ionizable surfactant is the ionized form of a surfactant selected from the group consisting of lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholate, taurocholate, glycocholate, deoxycholate, chenodeoxycholate, lithocholate, ursodeoxycholate, taurodeoxycholate, glycodeoxycholate, cholylsarcosine, caproate, caprylate, caprate, laurate, oleate, lauryl sulfate, docusate, lauroyl carnitine, palmitoyl carnitine, myristoyl carnitine, and salts and mixtures thereof.

6. The pharmaceutical system of claim 2, wherein the ionized ionizable surfactant is the ionized form of a surfactant selected from the group consisting of lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, chenodeoxycholate, lithocholate, ursodeoxycholate, taurocholate, caprylate, caprate, oleate, lauryl sulfate, docusate, lauroyl carnitine, palmitoyl carnitine, myristoyl carnitine, and salts and mixtures thereof.

7. The pharmaceutical system of claim 1, wherein the hydrophilic surfactant comprises at least one non-ionic hydrophilic surfactant having an HLB value greater than or equal to about 10.

8. The pharmaceutical system of claim 7, wherein the non-ionic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene vegetable oils; polyoxyethylene hydrogenated vegetable oils; reaction products of polyols and at least one member of the group consisting of fatty acids, glycerides, vegetable oils, and hydrogenated vegetable oils; sugar esters, sugar ethers; sucroglycerides; and mixtures thereof.

9. The pharmaceutical system of claim 7, wherein the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene vegetable oils; polyoxyethylene hydrogenated vegetable oils; reaction products of polyols and at least one member of the group consisting of fatty acids, glycerides, vegetable oils, and hydrogenated vegetable oils; and mixtures thereof.

10. The pharmaceutical system of claim 9, wherein the non-ionic hydrophilic surfactant is the reaction product of a polyol and a monoglyceride, diglyceride, triglyceride, or a mixture thereof.

11. The pharmaceutical system of claim 10, wherein the reaction product comprises a transesterification product.

12. The pharmaceutical system of claim 10, wherein the polyol is glycerol, ethylene glycol, polyethylene glycol, sorbitol, propylene glycol, pentaerythritol, a saccharide, or a mixture thereof.

13. The pharmaceutical system of claim 7, wherein the hydrophilic surfactant is selected from the group consisting of PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG40 stearate, PEG-100 stearate, PEG-20 dilaurate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate monoglycerides, PEG-6 caprate/caprylate diglycerides, PEG-8 caprate/caprylate monoglycerides, PEG -8 caprate/caprylate diglycerides, polyglyceryl-10 laurate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, and combinations thereof.

14. The pharmaceutical system of claim 7, wherein the hydrophilic surfactant is selected from the group consisting of PEG-20 laurate, PEG-20 oleate, PEG-35 castor oil, PEG-40 palm kernel oil, PEG-40 hydrogenated castor oil, PEG-60 corn oil, polyglyceryl-10 laurate, PEG-6 caprate/caprylate monoglycerides, PEG-6 caprate/caprylate diglycerides, PEG-8 caprate/caprylate monoglycerides, PEG-8 caprate/caprylate diglycerides, polysorbate 20, polysorbate 80, POE-9 lauryl ether, POE-23 lauryl ether, POE-10 oleyl ether, sucrose monostearate, sucrose monolaurate, a poloxamer, and combinations thereof.

15. The pharmaceutical system of claim 7, wherein the hydrophilic surfactant is selected from the group consisting of PEG-35 castor oil, PEG-40 hydrogenated castor oil, PEG-60 corn oil, PEG-6 caprate/caprylate monoglycerides, PEG-6 caprate/caprylate diglycerides, PEG-8 caprate/caprylate monoglycerides, PEG-8 caprate/caprylate diglycerides, polysorbate 20, polysorbate 80, tocopheryl PEG-1000 succinate, a poloxamer, and combinations thereof.

16. The pharmaceutical system of claim 1, wherein the composition comprises at least two hydrophilic surfactants.

17. The pharmaceutical system of claim 1, wherein the hydrophobic surfactant comprises an un-ionized ionizable surfactant.

18. The pharmaceutical system of claim 17, wherein the un-ionized ionizable surfactant is the un-ionized form of a surfactant selected from the group consisting of bile acids and analogues and derivatives thereof; carnitine fatty acid esters; alkylsulfates; fatty acids; acyl lactylates; mono-acetylated tartaric acid esters of mono- and diglycerides, diacetylated tartaric acid esters of mono- and diglycerides; succinylated monoglycerides; citric acid esters of mono- and diglycerides; and mixtures thereof.

19. The pharmaceutical system of claim 17 wherein the un-ionized ionizable surfactant is the un-ionized form of a surfactant selected from the group consisting of lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholic acid, taurocholic acid, glycocholic acid, deoxycholic acid, taurodeoxycholic acid, chenodeoxycholic acid, glycodeoxycholic acid, glycochenodeoxycholic acid, taurochenodeoxycholic acid, ursodeoxycholic acid, lithocholic acid, tauroursodeoxycholic acid, glycoursodeoxycholic acid, cholylsarcosine, N-methyl taurocholic acid, caproic acid, caprylic acid, capric acid, lauric acid, myristic acid, palmitic acid, oleic acid, ricinoleic acid, linoleic acid, linolenic acid, stearic acid, lauryl sulfate, tetraacetyl sulfate, lauroyl carnitine, palmitoyl carnitine, myristoyl carnitine, and mixtures thereof.

20. The pharmaceutical system of claim 17, wherein the un-ionized ionizable surfactant is the unionized form of a surfactant selected from the group consisting of lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholic acid, taurocholic acid, glycocholic acid, deoxycholic acid, chenodeoxycholic acid, lithocholic acid, ursodeoxycholic acid, taurodeoxycholic acid, glycodeoxycholic acid, cholylsarcosine, caproic acid, caprylic acid, capric acid, lauric acid, oleic acid, lauryl sulfate, lauroyl carnitine, palmitoyl carnitine, myristoyl carnitine, and mixtures thereof.

21. The pharmaceutical system of claim 17, wherein the un-ionized ionizable surfactant is the un-ionized form of a surfactant selected from the group consisting of lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, chenodeoxycholic acid, lithocholic acid, ursodeoxycholic acid, taurocholic acid, caprylic acid, capric acid, oleic acid, lauryl sulfate, docusate, lauroyl carnitine, palmitoyl carnitine, myristoyl carnitine, and mixtures thereof.

22. The pharmaceutical system of claim 1, wherein the hydrophobic surfactant comprises at least one surfactant having an HLB value less than about 10.

23. The pharmaceutical system of claim 22, wherein the hydrophobic surfactant is selected from the group consisting of alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono- and diglycerides; propylene glycol diglycerides; sorbitan fatty acid esters; polyoxyethylene sorbitan fatty acid esters; polyoxyethylene-polyoxypropylene block copolymers; transesterified vegetable oils; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, and hydrogenated vegetable oils; and mixtures thereof.

24. The pharmaceutical system of claim 22, wherein the hydrophobic surfactant is selected from the group consisting of fatty acids; bile acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono- and diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; reaction products of polyols and at least one member of the group consisting of fatty acids, glycerides, vegetable oils, and hydrogenated vegetable oils; and mixtures thereof.

25. The pharmaceutical system of claim 22, wherein the hydrophobic surfactant is selected from the group consisting of bile acids; lower alcohol fatty acids esters; polypropylene glycol fatty acid esters; propylene glycol fatty acid esters; glycerol fatty acid esters; acetylated glycerol fatty acid esters; lactic acid derivatives of mono- and diglycerides; sorbitan fatty acid esters; polyoxyethylene vegetable oils; and mixtures thereof.

26. The pharmaceutical system of claim 22, wherein the hydrophobic surfactant is a glycerol fatty acid ester selected from the group consisting of glycerol fatty acid monoesters, glycerol fatty acid diesters, acetylated glycerol fatty acid monoesters, acetylated glycerol fatty acid diesters, or a mixture thereof.

27. The pharmaceutical system of claim 26, wherein the glycerol fatty acid ester is selected from the group consisting of glycerol fatty acid monoesters, glycerol fatty acid diesters, and mixtures thereof.

28. The pharmaceutical system of claim 27, wherein the fatty acid of the glycerol fatty acid ester is a $C_6$ to $C_{22}$ fatty acid or a mixture thereof.

29. The pharmaceutical system of claim 22, wherein the hydrophobic surfactant is a reaction product of a polyol and at least one member of the group consisting of fatty acids, glycerides, vegetable oils, and hydrogenated vegetable oils.

30. The pharmaceutical system of claim 29, wherein the reaction product is a transesterification product of a polyol and at least one member of the group consisting of fatty acids, glycerides, vegetable oils, and hydrogenated vegetable oils.

31. The pharmaceutical system of claim 29, wherein the polyol is polyethylene glycol, sorbitol, propylene glycol, pentaerythritol, a saccharide, or a mixture thereof.

32. The pharmaceutical system of claim 22, wherein the hydrophobic surfactant is selected from the group consisting of myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{22}$ fatty acid; monoglycerides of a $C_6$ to $C_{22}$ fatty acid; acetylated monoglycerides of $C_6$ to $C_{22}$ fatty acid; diglycerides of $C_6$ to $C_{22}$ fatty acids; lactic acid derivatives of monoglycerides; lactic acid derivatives of diglycerides; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; cholic acid; ursodeoxycholic acid; glycocholic acid; taurocholic acid; lithocholic acid; deoxycholic acid; chenodeoxycholic acid; and mixtures thereof.

33. The pharmaceutical system of claim 22, wherein the hydrophobic surfactant is selected from the group consisting of myristic acid; oleic acid; lauric acid; stearic acid; palmitic acid, PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG-3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; mono, di, tri, tetra esters vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-3 distearate; propylene glycol mono- or diesters of a $C_6$ to $C_{22}$ fatty acid; monoglycerides of a $C_6$ to $C_{22}$ fatty acid; acetylated monoglycerides of $C_6$ to $C_{22}$ fatty acid; diglycerides of $C_6$ to $C_{22}$ fatty acids; laetic acid derivatives of monoglycerides; lactic acid derivatives of diglycerides; PEG-6 sorbitan tetra, hexastearate; PEG-6 sorbitan tetraoleate; sorbitan monolaurate; sorbitan monopalmitate; sorbitan monooleate; sorbitan monostearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; cholic acid; ursodeoxycholic acid; glycocholic acid; taurocholic acid; lithocholic acid; deoxycholic acid; chenodeoxycholic acid; and mixtures thereof.

34. The pharmaceutical system of claim 1, wherein each of the at least two surfactants is selected from the group consisting of sodium lauryl sulfate, oleic acid, linoleic acid, monoolein, deoxycholate, taurodeoxycholate, glycochenodeoxycholate, polyoxyethylene X-lauryl ether, where X is from 9 to 20, sodium tauro-24,25-dihydrofusidate, polyoxyethylene ether, polyoxyethylene sorbitan esters, p-t-octylphenoxypolyoxyethylene, N-lauryl-β-D-maltopyranoside, and 1-dodecylazacycloheptane-2-azone, and is present in an amount of greater than 10% by weight, based on the total weight of the pharmaceutical system.

35. The pharmaceutical system of claim 1, wherein the hydrophilic therapeutic agent is a drug, a vitamin, a nutritional supplement, a cosmeceutical, a diagnostic agent, or a mixture thereof.

36. The pharmaceutical system of claim 1, wherein the hydrophilic therapeutic agent has an apparent water solubility of at least about 1 mg/mL.

37. The pharmaceutical system of claim 1, wherein the hydrophilic therapeutic agent is a hydrophilic drug, a cytokine, a peptidomimetic, a peptide, a protein, a toxoid, a serum, an antibody, a vaccine, a nucleoside, a nucleotide, a portion of genetic material, a nucleic acid, or a mixture thereof.

38. The pharmaceutical system of claim 1, wherein the hydrophilic therapeutic agent is selected from the hydrophilic members of the group consisting of analgesics, anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytic, sedatives, hypnotics, neuroleptics, β-Blockers, cardiac inotropic agents, corticosteriods, diuretics, anti-parkinsonian agents, gastro-intestinal agents, histamine $H_1$-receptor antagonists, keratolytics, lipid regulating agents, muscle relaxants, anti-anginal agents, nutritional agents, analgesics, sex hormones, stimulants, cytokines, peptidomimetics, peptides, proteins, toxoids, sera, antibodies, vaccines, nucleosides, nucleotides, genetic material, nucleic acids, and mixtures thereof.

39. The pharmaceutical system of claim 1, wherein the hydrophilic therapeutic agent is selected from the group consisting of acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime; cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; dornase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor; granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine; menotropins; mephenzolate bromide; mesalmine; methanamine; methotrexate; methscopolamine; metformin hydrochloride; metroprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine; vinorelbine; vitamin B12; warfarin sodium; yellow fever vaccine; zalcitabine; zanamavir; zolandronate; and zidovudine.

40. The pharmaceutical system of claim 1, wherein the hydrophilic therapeutic agent is selected from the group consisting of acarbose; acyclovir; atracurium besylate; alendronate; alglucerase; amantadine hydrochloride; amphotericin B; antihemophilic factor (human); antihemophilic factor (porcine); antihemophilic factor (recombinant; azithromycin; calcitonin human; calcitonin salmon; capecitabine; cefazolin sodium; cefonicid sodium; cefoperazone; cefoxitin sodium; ceftizoxime; ceftriaxone; cefuiroxime axetil; cephalexin; chrionic gonadotropin; cidofovir; cladribine; clindamycin and clindamycin derivatives; cortocotropin; cosyntropin; cromalyn sodium; cytarabine; daltaperin sodium; danaproid; desmopressin; didanosine; dirithromycin; editronate disodium; enoxaprin sodium; epoetin alpha; factor IX; farmiciclovir; fluradabine; foscarnet sodium; ganciclovir; granulocyte colony stimulating factor; granulocyte-macrophage stimulating factor; growth hormones-recombinant human; growth hormone-Bovine; gentamycin; glucagon; gonadotropin releasing hormone and synthetic analogs thereof; GnRH; gonadorelin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; lamivudine; leucovorin calcium; leuprolide acetate; lincomycin and lincomycin derivatives; metforrmin hydrochloride; nedocromil sodium; neostigmine bromide; neostigmine methyl sulfate; neutontin; octreotide acetate; olpadronate; pamidronate disodium; pancuronium bromide; pentamindine isethionate; pentagastrin; physostigmine salicylate; poliovirus vaccine live (OPV); pyridostigmine bromide; residronate; ribavarin; rimantadine hydrochloride; rotavirus vaccine; salmetrol xinafoate; somatostatin; spectinomycin; stavudine; streptokinase; ticarcillin; tiludronate; tissue type plasminogen activator; TNFR:Fc; TNK-tPA; trimetrexate gluconate; trospectinomycin; tumor necrosis factor; typhoid vaccine live; urokinase; vancomycin; valaciclovir; vasopressin and vasopressin derivatives; vinblastin; vincristine; vinorelbine; warfarin sodium; zalcitabine; zanamavir; and zidovudine.

41. The pharmaceutical system of claim 1, wherein the hydrophilic therapeutic agent is selected from the group consisting of acarbose; alendronate; amantadine hydrochloride; azithromycin; calcitonin human; calcitonin salmon; ceftriaxone; cefuroxime axetil; chrionic gonadotropin; cromalyn sodium; daltaperin sodium; danaproid; desmopressin; didanosine; editronate disodium; enoxaprin sodium; epoetin alpha; factor IX; famiciclovir; foscarnet sodium; ganciclovir; granulocyte colony stimulating factor; granulocyte-macrophage stimulating factor; growth hormones-recombinant human; growth hormone-Bovine; glucagon; gonadotropin releasing hormone and synthetic analogs thereof; GnRH; gonadorelin; heparin sodium; indinavir sulfate; influenza virus vaccine; interleukin-2; interleukin-3; insulin-human; insulin lispro; insulin procine interferon alpha; interferon beta; leuprolide acetate; metformin hydrochloride; nedocromil sodium; neostigmine bromide; neostigmine methyl sulfate; neutontin; octreotide acetate; olpadronate; pamidronate disodium; residronate; rimantadine hydrochloride; salmetrol xinafoate; somatostatin; stavudine; ticarcillin; tiludronate; tissue type plasminogen activator; TNFR:Fc; TNK-tPA; tumor necrosis factor; typhoid vaccine live; vancomycin; valaciclovir; vasopressin and vasopressin derivatives; zalcitabine; zanamavir and zidovudine.

42. The pharmaceutical system of claim 1, wherein the composition further includes at least one pharmaceutical additive selected from the group consisting of an antioxidanl, a bufferant, an antifoaming agent, a detackifier, a preservative, a chelating agent, a viscomodulator, a tonicifier, a flavorant, a colorant, an odorant, an opacifier, a suspending agent, a binder, a filler, a plasticizer, a lubricant, an enzyme inhibiting agent, and combinations thereof.

43. The pharmaceutical system of claim 42, wherein the composition includes an enzyme inhibiting agent present in an amount sufficient to at least partially inhibit enzymatic degradation of the hydrophilic therapeutic agent.

44. The pharmaceutical system of claim 43, wherein the enzyme inhibiting agent is P-aminobenzamidine, FK-448, camostat mesylate, sodium glycocholate, an amino acid, a modified amino acid, a peptide, a modified peptide, a polypeptide protease inhibitor, a complexing agent, a mucoadhesive polymer, a polymer-inhibitor conjugate, or a mixture thereof.

45. The pharmaceutical system of claim 44, wherein the enzyme inhibiting agent is selected from the group consisting of P-aminobenzamidine, FK-448, camostat mesylate, sodium glycocholate, aminoboronic acid derivatives, n-acetylcysteine, bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, amastatin, protinin, Bowman-Birk inhibitor, soybean trypsin inhibitor, chicken egg white trypsin inhibitor, chicken ovoinhibitor, human pancreatic trypsin inhibitor, EDTA, EGTA, 1,10-phenanthroline, hydroxychinoline, polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bowman-Birk inhibitor, and mixtures thereof.

46. The pharmaceutical system of claim 1, wherein the composition further comprises a pharmaceutically acceptable acid.

47. The pharmaceutical system of claim 46, wherein the acid is selected from the group consisting of hydrochloric acid, hydrobromic acid, hydriodic acid, sulfuric acid, carbonic acid, nitric acid, boric acid, phosphoric acid, acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and mixtures thereof.

48. The pharmaceutical system of claim 1, wherein the composition further comprises a pharmaceutically acceptable base.

49. The pharmaceutical system of claim 48, wherein the base is an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid, or a mixture thereof.

50. The pharmaceutical system of claim 1, wherein the aqueous dispersion formed by the composition upon contact with an aqueous medium has an average particle size of less than about 200 nm upon mixing with an aqueous diluent.

51. The pharmaceutical system of claim 50, wherein the average particle size is less than about 100 nm.

52. The pharmaceutical system of claim 50, wherein the average particle size is less than about 50 nm.

53. The pharmaceutical system of claim 1, wherein the system is free of polyethylene glycol diesters.

54. The pharmaceutical system of claim 1, wherein the dosage form is free of water.

55. The pharmaceutical system of claim 1 in the form of a preconcentrate in a liquid, semi-solid, or solid form, or as an aqueous or organic diluted preconcentrate.

56. The pharmaceutical system of claim 1, wherein the dosage form of the composition is processed by balling, lyophilization, encapsulation, extruding, compression, melting, molding, spraying, spray congealing, coating, comminution, mixing, cryopelletization, spheronization, homogenization, sonication, granulation, or a combination thereof.

57. The pharmaceutical system of claim 1, wherein the dosage form of the composition is a pill, capsule, caplet, tablet, granule, pellet, bead or powder.

58. The pharmaceutical system of claim 1, wherein the dosage form of the composition is a starch capsule, a cellulosic capsule, a hard gelatin capsule or a soft gelatin capsule.

59. The pharmaceutical system of claim 1, wherein the dosage form is formulated for immediate release, controlled release, extended release, delayed release, targeted release, or targeted delayed release.

60. The pharmaceutical system of claim 57, coated with at least one enteric coating, seal coating, extended release coating, or targeted delayed release coating.

61. The pharmaceutical system of claim 60, wherein the coating is comprised of a material selected from the group consisting of shellac, acrylic polymers, cellulosic derivatives, polyvinyl acetate phthalate, and mixtures thereof.

62. The pharmaceutical system of claim 60, herein the coating is comprised of a material selected from the group consisting of acrylic acid and methacrylic acid resins, cellulose acetate phthalate, cellulose acetate trimellitate, ethyl cellulose, hydroxypropyl methyl cellulose phthalate, hydroxypropyl methyl cellulose succinate, polyvinylacetate phthalate, and mixtures thereof.

63. The pharmaceutical system of claim 60, wherein the coating is comprised of a material selected from the group consisting of acrylic acid and methacrylic acid resins, cellulose acetate phthalate, ethyl cellulose, hydroxypropyl methyl cellulose phthalate, hydroxypropyl methyl cellulose succinate, polyvinylacetate phthalate, and mixtures thereof.

64. The pharmaceutical system of claim 1, wherein the dosage form of the composition is a solution, suspension, emulsion, cream, ointment, lotion, suppository, spray, aerosol, paste, gel, drops, douche, ovule, wafer, troche, cachet, syrup or elixir.

65. The pharmaceutical system of claim 1, wherein the dosage form is a multiparticulate carrier coated onto a substrate with the composition.

66. The pharmaceutical system of claim 65, wherein the substrate is a particle, a granule, a pellet or a bead, and is formed of the therapeutic agent, a pharmaceutically acceptable material, or a mixture thereof.

67. The pharmaceutical system of claim 65, wherein the multiparticulate carrier is coated with at least one enteric coating, seal coating, extended release coating, or targeted delayed release coating.

68. The pharmaceutical system of claim 65, wherein the dosage form is further processed by encapsulation, compression, extrusion, molding, spheronization or cryopelletization.

69. The pharmaceutical system of claim 65, wherein the dosage form is further processed to form a starch capsule, a cellulosic capsule, a hard gelatin capsule, or a soft gelatin capsule.

70. The pharmaceutical system of claim 69, wherein the capsule is coated with at least one enteric coating, seal coating, extended release coating, or targeted delayed release coating.

71. The pharmaceutical system of claim 1, wherein the hydrophilic therapeutic agent is present in the dosage form.

72. The pharmaceutical system of claim 71, wherein the hydrophilic therapeutic agent is solubilized in the composition, suspended in the composition, or partially solubilized and partially suspended in the composition.

73. The pharmaceutical system of claim 1, wherein the hydrophilic therapeutic agent is present in a second dosage form separate from the dosage form containing the absorption enhancing composition.

74. The pharmaceutical system of claim 1, wherein the dosage form of the composition is formulated for oral, mucosal, nasal, pulmonary, vaginal, transmembrane, buccal or rectal administration.

75. The pharmaceutical system of claim 73, wherein the dosage form of the hydrophilic therapeutic agent is formulated for oral, mucosal, nasal, pulmonary, vaginal, transmembrane, buccal or rectal administration.

76. A pharmaceutical system for enhanced absorption of a hydrophilic therapeutic agent, the system consisting essentially of:
  (a) a dosage form of an absorption enhancing composition, the composition comprising:
    (i) at least one hydrophilic surfactant selected from the group consisting of ionized surfactants, non-ionic hydrophilic surfactants having an HLB value greater than or equal to about 10, and combinations thereof,
    (ii) at least one hydrophobic surfactant selected from the group consisting of hydrophobic (a) alcohols, polyoxyethylene alkylethers, bile acids, glycerol fatty acid monoesters, glycerol fatty acid diesters, acetylated glycerol fatty acid monoesters, acetylated glycerol fatty acid diesters, lower alcohol fatty acid monoesters, lower alcohol fatty acid diesters, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, un-ionized (b) fatty acids, carnitine fatty acid esters, alkylsulfates, acyl lactylates, mono-acetylated tartaric acid esters of mono- and diglycerides, diacetylated tartaric acid esters of mono- and diglycerides, succinylated monoglycerides, citric acid esters of mono- and diglycerides, and mixtures thereof, wherein the hydrophilic and hydrophobic surfactants are present in amounts such that upon mixing with an aqueous diluent at 100× dilution, the composition forms an aqueous dispersion having an average particle size of less than about 200 nm, and
    (iii) at least one solubilizer; and
  (b) a therapeutically effective amount of a hydrophilic therapeutic agent, wherein the pharmaceutical system is free of triglycerides.

77. The pharmaceutical system of claim 76, wherein the hydrophilic surfactant comprises at least one ionized ionizable surfactant.

78. The pharmaceutical system of claim 77, wherein the ionized ionizable surfactant is the ionized form of a surfactant selected from the group consisting of bile acids and salts, analogues, and derivatives thereof; lecithins, lysolecithin, phospholipids, lysophospholipids and derivatives thereof; carnitine fatty acid ester salts; salts of alkylsulfates; salts of fatty acids; sodium docusate; acyl lactylates; mono-acetylated tartaric acid esters of mono- and diglycerides, diacetylated tartaric acid esters of mono- and diglycerides; succinylated monoglycerides; citric acid esters of mono- and diglycerides; and mixtures thereof.

79. The pharmaceutical system of claim 77, wherein the ionized ionizable surfactant is the ionized form of a surfactant selected from the group consisting of lecithin, lysolecithin, phosphatidylcholine, phosphatidylethanolamine, phosphatidylglycerol, phosphatidic acid, phosphatidylserine, lysophosphatidylcholine, lysophosphatidylethanolamnine, lysophosphatidylglycerol, lysophosphatidic acid, lysophosphatidylserine, PEG-phosphatidyletanolamine, PVP-phosphatidyletanolamine, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholate, taurocholate, glycocholate, deoxycholate, taurodeoxychorate, chenodeoxycholate, glycodeoxycholate, glycochenodeoxycholate, taurochenodeoxycholate, ursodeoxycholate, lithocholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, tetraacetyl sulfate, docusate, lauroyl carnitine, palmitoyl carnitine, myristoyl carnitine, and salts and mixtures thereof.

80. The pharmaceutical system of claim 77, wherein the ionized ionizable surfactant is the ionized form of a surfactant selected from the group consisting of lecithin, lysolecithin, phosphatidylcholine, phosphatidylethanolamine, phosphatidylglycerol, lysophosphatidylcholine, PEG-phosphatidyletanolamine, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholate, taurocholate, glycocholate, deoxycholate, chenodeoxycholate, lithocholate, ursodeoxycholate, taurodeoxycholate, glycodeoxycholate, cholylsarcosine, caproate, caprylate, caprate, laurate, oleate, lauryl sulfate, docusate, lauroyl carnitine, palmitoyl carnitine, myristoyl carnitine, and salts and mixtures thereof.

81. The pharmaceutical system of claim 77, wherein the ionized ionizable surfactant is the ionized form of a surfactant selected from the group consisting of lecithin, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, chenodeoxycholate, lithocholate, ursodeoxycholate, taurocholate, caprylate, caprate, oleate, lauryl sulfate, docusate, lauroyl carnitine, palmitoyl carnitine, myristoyl carnitine, and salts and mixtures thereof.

82. The pharmaceutical system of claim 76, wherein the hydrophilic surfactant comprises at least one non-ionic hydrophilic surfactant having an HLB value greater than or equal to about 10.

83. The pharmaceutical system of claim 82, wherein the non-ionic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; sugar esters, sugar ethers; sucroglycerides; and mixtures thereof.

84. The pharmaceutical system of claim 82, wherein the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

85. The pharmaceutical system of claim 84, wherein the non-ionic hydrophilic surfactant is the reaction product of a polyol and a monoglyceride, diglyceride, triglyceride, or a mixture thereof.

86. The pharmaceutical system of claim 85, wherein the reaction product comprises the transesterification product of a polyol and at least one member of the group consisting of fatty acids, glycerides, vegetable oils, hydrogenated vegetable oils, and sterols.

87. The pharmaceutical system of claim 85, wherein the polyol is glycerol, ethylene glycol, polyethylene glycol, sorbitol, propylene glycol, pentaerythritol, a saccharide, or a mixture thereof.

88. The pharmaceutical system of claim 82, wherein the hydrophilic surfactant is selected from the group consisting of PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG40 stearate, PEG-100 stearate, PEG-20 dilaurate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG40 glyceryl laurate, PEG-40 palm kernel oil, PEG-50 hydrogenated castor oil, PEG-40 castor oil, PEG-35 castor oil, PEGG-60 castor oil, PEG-40 hydrogenated castor oil, PEG-60 hydrogenated castor oil, PEG-60 corn oil, PEG-6 caprate/caprylate monoglycerides, PEG-6 caprate/caprylate diglycerides, PEG-8 caprate/caprylate monoglycerides, PEG-8 caprate/caprylate diglycerides, polyglyceryl-10 laurate, PEG-30 cholesterol, PEG-25 phyto sterol, PEG-30 soya sterol, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, aid combinations thereof.

89. The pharmaceutical system of claim 82, wherein the hydrophilic surfactant is selected from the group consisting of PEG-20 laurate, PEG-20 oleate, PEG-35 castor oil, PEG-40 palm kernel oil, PEG-40 hydrogenated castor oil, PEG-60 corn oil, polyglyceryl-10 laurate, PEG-6 caprate/caprylate monoglycerides, PEG-6 caprate/caprylate diglycerides, PEG-8 caprate/caprylate monoglycerides, PEG-8 caprate/caprylate diglycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate, a poloxamer, and combinations thereof.

90. The pharmaceutical system of claim 82, wherein the hydrophilic surfactant is selected from the group consisting of PEG-35 castor oil, PEG-40 hydrogenated castor oil, PEG-60 corn oil, PEG-6 caprate/caprylate monoglycerides, PEG-6 caprate/caprylate diglycerides, PEG-8 caprate/caprylate monoglycerides, PEG-8 caprate/caprylate diglycerides, polysorbate 20, polysorbate 80, tocopheryl PEG-1000 succinate, PEG-24 cholesterol, a poloxamer, and combinations thereof.

91. The pharmaceutical system of claim 76, wherein the composition comprises at least two hydrophilic surfactants.

92. The pharmaceutical system of claim 76, wherein the hydrophobic surfactant comprises an un-ionized ionizable surfactant.

93. The pharmaceutical system of claim 92, wherein the un-ionized ionizable surfactant is the un-ionized form of a surfactant selected from the group consisting of bile acids and analogues and derivatives thereof; lecithins, lysolecithin, phospholipids, lysophospholipids and derivatives thereof; carnitine fatty acid esters; alkylsulfates; fatty acids; acyl lactylates; mono-acetylated tartaric acid esters of mono- and diglycerides, diacetylated tartaric acid esters of mono- and diglycerides; succinylated monoglycerides; citric acid esters of mono- and diglycerides; and mixtures thereof.

94. The pharmaceutical system of claim 92, wherein the un-ionized ionizable surfactant is the un-ionized form of a surfactant selected from the group consisting of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholic acid, taurocholic acid, glycocholic acid, deoxycholic acid, taurodeoxycholic acid, chenodeoxycholic acid, glycodeoxycholic acid, glycochenodeoxycholic acid, taurochenodeoxycholic acid, ursodeoxycholic acid, lithocholic acid, tauroursodeoxycholic acid, glycoursodeoxycholic acid, cholylsarcosine, N-methyl taurocholic acid, caproic acid, caprylic acid, capric acid, lauric acid, myristic acid, palmitic acid, oleic acid, ricinoleic acid, linoleic acid, linolenic acid, stearic acid, lauryl sulfate, tetraacetyl sulfate, lauroyl carnitine, palmitoyl carnitine, myristoyl carnitine, and mixtures thereof.

95. The pharmaceutical system of claim 92, wherein the un-ionized ionizable surfactant is the unionized form of a surfactant selected from the group consisting of lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, cholic acid, taurocholic acid, glycocholic acid, deoxycholic acid, chenodeoxycholic acid, lithocholic acid, ursodeoxycholic acid, taurodeoxycholic acid, glycodeoxycholic acid, cholylsarcosine, caproic acid, caprylic acid, capric acid, lauric acid, oleic acid, lauryl sulfate, lauroyl carnitine, palmitoyl carnitine, myristoyl carnitine, and mixtures thereof.

96. The pharmaceutical system of claim 92, wherein the un-ionized ionizable surfactant is the un-ionized form of a surfactant selected from the group consisting of lecithin, lactylic esters of fatty acids, stearoyl-2-lactylate, stearoyl lactylate, succinylated monoglycerides, mono-acetylated tartaric acid esters of mono- and diglycerides, diacetylated tartaric acid esters of mono- and diglycerides, citric acid esters of mono- and diglycerides, chenodeoxycholic acid, lithocholic acid, ursodeoxycholic acid, taurocholic acid, caprylic acid, capric acid, oleic acid, lauryl sulfate, docusate, lauroyl carnitine, palmitoyl carnitine, myristoyl carnitine, and mixtures thereof.

97. The pharmaceutical system of claim 92 wherein the hydrophobic surfactant comprises at least one surfactant having an HLB value less than about 10.

98. The pharmaceutical system of claim 97, wherein the hydrophobic surfactant is selected from the group consisting of alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono- and diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

99. The pharmaceutical system of claim 97, wherein the hydrophobic surfactant is selected from the group consisting of fatty acids; bile acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono- and diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

100. The pharmaceutical system of claim 97, wherein the hydrophobic surfactant is selected from the group consisting of bile acids; lower alcohol fatty acids esters; polypropylene glycol fatty acid esters; propylene glycol fatty acid esters; glycerol fatty acid esters; acetylated glycerol fatty acid esters; lactic acid derivatives of mono- and diglycerides; sorbitan fatty acid esters; polyoxyethylene vegetable oils; and mixtures thereof.

101. The pharmaceutical system of claim 97, wherein the hydrophobic surfactant is a glycerol fatty acid ester selected from the group consisting of glycerol fatty acid monoesters, glycerol fatty acid diesters, acetylated glycerol fatty acid monoesters, acetylated glycerol fatty acid diesters, and mixtures thereof.

102. The pharmaceutical system of claim 97, wherein the glycerol fatty acid ester is selected from the group consisting of glycerol fatty acid monoesters, glycerol fatty acid diesters, and mixtures thereof.

103. The pharmaceutical system of claim 102, wherein the fatty acid of the glycerol fatty acid ester is a $C_6$ to $C_{22}$ fatty acid or a mixture thereof.

104. The pharmaceutical system of claim 97, wherein the hydrophobic surfactant is a reaction product of a polyol and at least one member of the group consisting of fatty acids, glycerides, vegetable oils, hydrogenated vegetable oils, and sterols.

105. The pharmaceutical system of claim 104, wherein the reaction product is a transesterification product of a polyol and at least one member of the group consisting of fatty acids, glycerides, vegetable oils, hydrogenated vegetable oils, and sterols.

106. The pharmaceutical system of claim 105, wherein the hydrophobic surfactant is selected from the group consisting of myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{22}$ fatty acid; monoglycerides of a $C_6$ to $C_{22}$ fatty acid; acetylated monoglycerides of $C_6$ to $C_{22}$ fatty acid; diglycerides of $C_6$ to $C_{22}$ fatty acids; lactic acid derivatives of monoglycerides; lactic acid derivatives of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; PEG 2-4 lauryl ether; PEG-2 cetyl ether; PEG-2 stearyl ether; sucrose.

107. The pharmaceutical system of claim 97, wherein the hydrophobic surfactant is selected from the group consisting of myristic acid; oleic acid; lauric acid; stearic acid; palmitic acid; PEG 1-4 stearate; PEG 24 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PETG 6-20 almond oil; PEG-6 olive oil; PEG-6 peanut oil; PEG-6 palm kernel oil; PEG-6 hydrogenated palm kernel oil; mono, di, tri, tetra esters of vegetable oil and sorbitol; pentaerythrityl di, tetra stearate, isostearate, oleate, caprylate, or caprate; polyglyceryl 2-4 oleate, stearate, or isostearate; polyglyceryl 4-10 pentaoleate polyglyceryl-3 dioleate; polyglyceryl-6 dioleate; polyglyceryl-3 distearate; propylene glycol mono- or diesters of a $C_6$ to $C_{22}$ fatty acid; monoglycerides of a $C_6$ to $C_{22}$ fatty acid; acetylated monoglycerides of $C_6$ to $C_{22}$ fatty acid; diglycerides or $C_6$ to $C_{22}$ fatty acids; lactic acid derivatives of monoglycerides; lactic acid derivatives of diglycerides; cholesterol; phytosterol: PEG 5-20 soya sterol; PEG-6 sorbitan tetra, hexastearate; PEG-6 sorbitan tetra-oleate; sorbitan monolaturate; sorbitan monopalmitate; sorbitan monooleate; sorbitan monostearate; sorbitan monoisostearate; sorbitan sesquioleate; sorbitan sesquistearate; PEG 2-5 oleyl ether; POE 2-4 lauryl ether; PFG-2 cetyl ether; PEG-2 stearyl ether; sucrose distearate; sucrose dipalmitate; ethyl oleate; isopropyl myristate; isopropyl palmitate; ethyl linoleate; isopropyl linoleate; poloxamers; cholic acid; ursodeoxycholic acid; glycocliolic acid; taurocliolic acid; lithocholic acid; deoxycholic acid; chenodeoxycholic acid; and mixtures thereof.

108. The pharmaceutical system of claim 97, wherein the hydrophobic surfactant is selected from the group consisting of oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; poloxamers; cholic acid; ursodeoxycholic acid; glycocholic acid; taurocholic acid; lithocholic acid; deoxycholic acid; chenodeoxycholic acid; and mixtures thereof.

109. The pharmaceutical system of claim 76, wherein the hydrophobic and hydrophilic surfactants are selected from the hydrophobic and hydrophilic members, respectively, of the group consisting of sodium lauryl sulfate, oleic acid, linoleic acid, monoolein, lecithin, lysolecithin, deoxycholate, taurodeoxycholate, glycochenodeoxycholate, polyoxyethylene X-lauryl ether, where X is from 9 to 20, sodium tauro-24,25-dihydrofusidate, polyoxyethylene ether, polyoxyethylene sorbitan esters, p-t-octylphenoxypolyoxyethylene, N-lauryl-β-D-maltopyranoside, 1-dodecylazacycloheptane-2-azone, and phospholipids, and are each present in an amount of greater than 10% by weight, based on the total weight of the pharmaceutical system.

110. The pharmaceutical system of claim 76, wherein the hydrophilic therapeutic agent is a drug, a vitamin, a nutritional supplement, a cosmeceutical, a diagnostic agent, or a mixture thereof.

111. The pharmaceutical system of claim 76, wherein the hydrophilic therapeutic agent has an apparent water solubility of at least about 1 mg/mL.

112. The pharmaceutical system of claim 76, wherein the hydrophilic therapeutic agent is a hydrophilic drug, a cytokine, a peptidomimetic, a peptide, a protein, a toxoid, a serum, an antibody, a vaccine, a nucleoside, a nucleotide, a portion of genetic material, a nucleic acid, or a mixture thereof.

113. The pharmaceutical system of claim 76, wherein the hydrophilic therapeutic agent is selected from the hydrophilic members of the group consisting of analgesics, anti-inflammatory agents, anthelmintics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytic, sedatives, hypnotics, neuroleptics, β-Blockers, cardiac inotropic agents, corticosteroids, diuretics, anti-parkinsonian agents, gastrointestinal agents, histamine $H_1$-receptor antagonists, keratolytics, lipid regulating agents, muscle relaxants, anti-anginal agents, nutritional agents, analgesics, sex hormones, stimulants, cytokines, peptidomimetics, peptides, proteins, toxoids, sera, antibodies, vaccines, nucleosides, nucleotides, genetic material, nucleic acids, and mixtures thereof.

114. The pharmaceutical system of claim 76, wherein the hydrophilic therapeutic agent is selected from the group consisting of acarbose; acyclovir; acetyl cysteine; acetylcholine chloride; alatrofloxacin; alendronate; alglucerase; amantadine hydrochloride; ambenomium; amifostine; amiloride hydrochloride; aminocaproic acid; amphotericin B; antihemophilic factor (human); antihemophilic factor (porcine); antihemophilic factor (recombinant); aprotinin; asparaginase; atenolol; atracurium besylate; atropine; azithromycin; aztreonam; BCG vaccine; bacitracin; becalermin; belladona; bepridil hydrochloride; bleomycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotoxime: cefoxitin sodium; ceftizoxime; ceftriaxone; cefuroxime axetil; cephalexin; cephapirin sodium; cholera vaccine; chrionic gonadotropin; cidofovir; cisplatin; cladribine; clidinium bromide; clindamycin and clindamycin derivatives; ciprofloxacin; clondronate; colistimethate sodium; colistin sulfate; cortocotropin; cosyntropin; cromalyn sodium; cytarabine; daltaperin sodium; danaproid; deforoxamine; denileukin diftitox; desmopressin; diatrizoate megluamine and diatrizoate sodium; dicyclomine; didanosine; dirithromycin; dopamine hydrochloride; domase alpha; doxacurium chloride; doxorubicin; editronate disodium; elanaprilat; enkephalin; enoxacin; enoxaprin sodium; ephedrine; epinephrine; epoetin alpha; erythromycin; esmol hydrochloride; factor IX; famiciclovir; fludarabine; fluoxetine; foscarnet sodium; ganciclovir; granulocyte colony stimulating factor, granulocyte-macrophage stimulating factor; growth hormones-recombinant human; growth hormone-bovine; gentamycin; glucagon; glycopyrolate; gonadotropin releasing hormone and synthetic analogs thereof; GnRH; gonadorelin; grepafloxacin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; japanese encephalitis virus vaccine; lamivudine; leucovorin calcium; leuprolide acetate; levofloxacin; lincomycin and lincomycin derivatives; lobucavir; lomefloxacin; loracarbef; mannitol; measles virus vaccine; meningococcal vaccine;

menotropins; mephenzolate bromide; mesalmine; methanamine; methotrexate; methscopolamine; metformin hydrochloride; metroprolol; mezocillin sodium; mivacurium chloride; mumps viral vaccine; nedocromil sodium; neostigmine bromide; neostigmine methyl sulfate; neutontin; norfloxacin; octreotide acetate; ofloxacin; olpadronate; oxytocin; pamidronate disodium; pancuronium bromide; paroxetine; pefloxacin; pentamindine isethionate; pentostatin; pentoxifylline; periciclovir; pentagastrin; phentolamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymixin B sulfate; pralidoxine chloride; pramlintide; pregabalin; propofenone; propenthaline bromide; pyridostigmine bromide; rabies vaccine; residronate; ribavarin; rimantadine hydrochloride; rotavirus vaccine; salmetrol xinafoate; sincalide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valaciclovir; valsartan; varicella virus vaccine live; vasopressin and vasopressin derivatives; vecoronium bromide; vinblastin; vincristine; vinorelbine; vitamin B12; warfarin sodium; yellow fever vaccine; zalcitabine; zanamavir; zolandronate; and zidovudine.

115. The pharmaceutical system of claim 76, wherein the hydrophilic therapeutic agent is selected from the group consisting of acarbose; acyclovir; atracurium besylate; alendronate; alglucerase; amantadine hydrochloride; amphotericin B; antihemophilic factor (human); antihemophilic factor (porcine); antihemophilic factor (recombinant; azithromycin; calcitonin human; calcitonin salmon; capecitabine; cefazolin sodium; cefonicid sodium; cefoperazone; cefoxitin sodium; ceftizoxime; ceftriaxone; cefuroxime axetil; cephalexin; chrionic gonadotropin; cidofovir; cladribine; clindamycin and clindamycin derivatives; cortocotropin; cosyntropin; cromalyn sodium; cytarabine; daltaperin sodium; danaproid; desmopressin; didanosine; dirithromycin; editronate disodium; enoxaprin sodium; epoetin alpha; factor IX; famiciclovir; fludarabine; foscarnet sodium; ganciclovir; granulocyte colony stimulating factor; granulocyte-macrophage stimulating factor; growth hormones-recombinant human; growth hormone-Bovine; gentamycin; glucagon; gonadotropin releasing hormone and synthetic analogs thereof; GnRH; gonadorelin; hemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; isofosfamide; lamivudine; leucovorin calcium; leuprolide acetate; lincomycin and lincomycin derivatives; metformin hydrochloride; nedocromil sodium; neostigmine bromide; neostigmine methyl sulfate; neutontin; octreotide acetate; olpadronate; pamidronate disodium; pancuronium bromide; pentamindine isethionate; pentagastrin; physostigmine salicylate; poliovirus vaccine live (OPV); pyridostigmine bromide; residronate; ribavarin; rimantadine hydrochloride; rotavirus vaccine; salmetrol xinafoate; somatostatin; spectinomycin; stavudine; streptokinase; ticarcillin; tiludronate; tissue type plasminogen activator; TNFR:Fc; TNK-tPA; trimetrexate gluconate; trospectinomycin; tumor necrosis factor; typhoid vaccine live; urokinase; vancomycin; valaciclovir; vasopressin and vasopressin derivatives; vinblastin; vincristine; vinorelbine; warfarin sodium; zalcitabine; zanamavir; and zidovudine.

116. The pharmaceutical system of claim 76, wherein the hydrophilic therapeutic agent is selected from the group consisting of acarbose; alendronate; amantadine hydrochloride; azithromycin; calcitonin human; calcitonin salmon; ceftriaxone; cefuiroxime axetil; chrionic gonadotropin; cromalyn sodium; daltaperin sodium; danaproid; desmopressin; didanosine; editronate disodium; enoxaprin sodium; epoetin alpha; factor IX; famiciclovir; foscarnet sodium; ganciclovir; granulocyte colony stimulating factor; granulocyte-macrophage stimulating factor; growth hormones-recombinant human; growth hormone-Bovine; glucagon; gonadotropin releasing hormone and synthetic analogs thereof; GnRH; gonadorelin; heparin sodium; indinavir sulfate; influenza virus vaccine; interleukin-2; interleukin-3; insulin-human; insulin lispro; insulin procine interferon alpha; interferon beta; leuprolide acetate; metformin hydrochloride; nedocromil sodium; neostigmine bromide; neostigmine methyl sulfate; neutontin; octreotide acetate; olpadronate; pamidronate disodium; residronate; rimantadine hydrochloride; salmetrol xinafoate; somatostatin; stavudine; ticarcillin; tiludronate; tissue type plasminogen activator; TNFR:Fc; TNK-tPA; tumor necrosis factor; typhoid vaccine live; vancomycin; valaciclovir; vasopressin and vasopressin derivatives; zalcitabine; zanamavir and zidovudine.

117. The pharmaceutical system of claim 76, wherein the solubilizer is selected from the group consisting of alcohols, polyols, amides, esters, propylene glycol ethers and mixtures thereof.

118. The pharmaceutical system of claim 76, wherein the composition further comprises includes at least one pharmaceutical additive selected from the group consisting of an antioxidant, a bufferant, an antifoaming agent, a detackifier, a preservative, a chelating agent, a viscomodulator, a tonicifier, a flavorant, a colorant, an odorant, an opacifier, a suspending agent, a binder, a filler, a plasticizer, a lubricant, an enzyme inhibiting agent, and combinations thereof.

119. The pharmaceutical system of claim 118, wherein the composition includes an enzyme inhibiting agent present in an amount sufficient to at least partially inhibit enzymatic degradation of the hydrophilic therapeutic agent.

120. The pharmaceutical system of claim 119, wherein the enzyme inhibiting agent is P-aminobenzamidine, FK-448, camostat mesylate, sodium glycocholate, an amino acid, a modified amino acid, a peptide, a modified peptide, a polypeptide protease inhibitor, a complexing agent, a mucoadhesive polymer, a polymer-inhibitor conjugate, or a mixture thereof.

121. The pharmaceutical system of claim 119, wherein the enzyme inhibiting agent is selected from the group consisting of P-aminobenzamidine, FK-448, camostat mesylate, sodium glycocholate, aminoboronic acid derivatives, n-acetylcysteine, bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, amastatin, protinin, Bowman-Birk inhibitor, soybean trypsin inhibitor, chicken egg white trypsin inhibitor, chicken ovoinhibitor, human pancreatic trypsin inhibitor, EDTA, EGTA, 1,10-phenanthroline, hydroxychinoline, polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bowman-Birk inhibitor, and mixtures thereof.

122. The pharmaceutical system of claim 76, wherein the composition further comprises a pharmaceutically acceptable acid.

123. The pharmaceutical system of claim 122, wherein the acid is selected from the group consisting of hydrochloric acid, hydrobromic acid, hydriodic acid, sulfuric acid, carbonic acid, nitric acid, boric acid, phosphoric acid, acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and mixtures thereof.

124. The pharmaceutical system of claim 76, wherein the composition further comprises a pharmaceutically acceptable base.

125. The pharmaceutical system of claim 124, wherein the base is an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid, or a mixture thereof.

126. The pharmaceutical system of claim 76, wherein the average particle size of the aqueous dispersion formed upon mixing the composition with an aqueous diluent is less than about 100 nm.

127. The pharmaceutical system of claim 126, wherein the average particle size is less than about 50 nm.

128. The pharmaceutical system of claim 76, wherein the composition forms a substantially optically clear aqueous dispersion having an absorbance of less than about 0.3 at 400 upon mixing with an aqueous diluent at 100× dilution.

129. The pharmaceutical system of claim 76, wherein the system is free of polyethylene glycol diesters.

130. The pharmaceutical system of claim 76, wherein the system is free of cholesterol.

131. The pharmaceutical system of claim 76, wherein the dosage form is free of water.

132. The pharmaceutical system of claim 76 in the form of a preconcentrate in a liquid, semi-solid, or solid form, or as an aqueous or organic diluted preconcentrate.

133. The pharmaceutical system of claim 76, wherein the dosage form of the composition is processed by balling, lyophilization, encapsulation, extruding, compression, melting, molding, spraying, spray congealing, coating, conmminution, mixing, cryopelletization, spheronization, homogenization, sonication, granulation, or a combination thereof.

134. The pharmaceutical system of claim 76, wherein the dosage form of the composition is a pill, capsule, caplet, tablet, granule, pellet, bead or powder.

135. The pharmaceutical system of claim 76, wherein the dosage form of the composition is a starch capsule, a cellulosic capsule, a hard gelatin capsule or a soft gelatin capsule.

136. The pharmaceutical system of claim 76, wherein the dosage form is formulated for immediate release, controlled release, extended release, delayed release, targeted release, or targeted delayed release.

137. The pharmaceutical system of claim 134, which further comprises at least one enteric coating, seal coating, extended release coating, or targeted delayed release coating.

138. The pharmaceutical system of claim 137, wherein the coating is comprised of a material selected from the group consisting of shellac, acrylic polymers, cellulosic derivatives, polyvinyl acetate phthalate, and mixtures thereof.

139. The pharmaceutical system of claim 137, wherein the coating is formed of a material selected from the group consisting of acrylic acid and methacrylic acid resins, cellulose acetate phthalate, cellulose acetate trimellitate, ethyl cellulose, hydroxypropyl methyl cellulose phthalate, hydroxypropyl methyl cellulose succinate, polyvinylacetate phthalate, and mixtures thereof.

140. The pharmaceutical system of claim 137, wherein the coating is formed of a material selected from the group consisting of acrylic acid and methacrylic acid resins, cellulose acetate phthalate, ethyl cellulose, hydroxypropyl methyl cellulose phthalate, hydroxypropyl methyl cellulose succinate, polyvinylacetate phthalate, and mixtures thereof.

141. The pharmaceutical system of claim 76, wherein the dosage form of the composition is a solution, suspension, emulsion, cream, ointment, lotion, suppository, spray, aerosol, paste, gel, drops, douche, ovule, wafer, troche, cachet, syrup or elixir.

142. The pharmaceutical system of claim 76, wherein the dosage form is a multiparticulate carrier coated onto a substrate with the composition.

143. The pharmaceutical system of claim 142, wherein the substrate is a particle, a granule, a pellet or a bead, and is formed of the therapeutic agent, a pharmaceutically acceptable material, or a mixture thereof.

144. The pharmaceutical system of claim 142, wherein the multiparticulate carrier is coated with at least one enteric coating, seal coating, extended release coating, or targeted delayed release coating.

145. The pharmaceutical system of claim 142, wherein the dosage form is further processed by encapsulation, compression, extrusion, molding, spheronization or cryopelletization.

146. The pharmaceutical system of claim 142, wherein the dosage form is further processed to form a starch capsule, a cellulosic capsule, a hard gelatin capsule, or a soft gelatin capsule.

147. The pharmaceutical system of claim 146, wherein the capsule is coated with at least one enteric coating, seal coating, extended release coating, or targeted delayed release coating.

148. The pharmaceutical system of claim 76, wherein the hydrophilic therapeutic agent is present in the dosage form.

149. The pharmaceutical system of claim 147, wherein the hydrophilic therapeutic agent is solubilized in the composition, suspended in the composition, or partially solubilized and partially suspended in the composition.

150. The pharmaceutical system of claim 76, wherein the hydrophilic therapeutic agent is present in a second dosage form separate from the dosage form containing the absorption enhancing composition.

151. The pharmaceutical system of claim 76, wherein the dosage form of the composition is formulated for oral, mucosal, pulmonary, nasal, vaginal, transmembrane, buccal or rectal administration.

152. The pharmaceutical system of claim 151, wherein the dosage form of the hydrophilic therapeutic agent is formulated for oral, mucosal, pulmonary, nasal, vaginal, transmembrane, buccal or rectal administration.

153. An absorption enhancing composition for co-administration to a patient with a hydrophilic therapeutic agent, the composition consisting essentially of an effective amount of am absorption enhancer comprising at least one hydrophilic surfactant selected from the group consisting of ionized surfactants, non-ionic hydrophilic surfactants having an HLB value greater than or equal to 10, mid combinations thereof, and at least cast one hydrophobic surfactant selected from the group consisting of hydrophobic (a) alcohols, polyoxyethylene alkylethers, bile acids, glycerol fatty acid monoesters, glycerol fatty acid diesters, acetylated glycerol fatty acid monoesters, acetylated glycerol fatty acid diesters, lower alcohol fatty acid monoesters, lower alcohol fatty acid diesters, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, soibitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction prodeucts of polyols and at least one member of the group consisting of fatty acids, glycerides, vegetable oils, and hydrogenated vegetable oils, and hydrophobic, un-ionized (b) fatty acids, carmitine fatty acid esters, alkylsulfates, acyl lactylates, mono-acetylated tartaric acid esters of mono- and diglycerides, diacetylated tartaric acid esters of mono- and diglycerides, succinylated monoglycerides, citric acid esters of mono- and diglycerides, and mixtures thereof, wherein the hydrophilic and hydrophobic surfactants are present in amounts such that upon mixing with an aqueous diluent the composition forms a clear aqueous dispersion having an absorbance of less than about 0.3 at 400 nm, the absorption enhancing composition being free of triglycerides.

154. The composition of claim 153, wherein the effective amount is an amount sufficient to increase the rate, the extent, or both the rate and extent, of bioabsorption of a hydrophilic therapeutic agent, when the composition and the hydrophilic therapeutic agent are administered to a patient.

155. The composition of claim 153, wherein the effective amount is an amount sufficient to improve the consistency of the rate, the extent, or both the rate and extent, of bioabsorption of a hydrophilic therapeutic agent, when the composition and the hydrophilic therapeutic agent are administered to a patient.

156. A method of controlling the rate, the extent, or both the rate ant extent of bioabsorption of a hydrophilic therapeutic agent administered to a patient, the method comprising:

(a) providing a dosage form of an absorption enhancing composition, the composition consisting essentially of at least one hydrophilic surfactant selected from the group consisting of ionized surfactants, non-ionic hydrophilic surfactants having an HLB value greater than or equal to 10, and combinations thereof, and at least one hydrophobic surfactant selected from the group consisting of hydrophobic (a) alcohols, polyoxyethylene alkylethers, bile acids, glycerol fatty acid monoesters, glycerol fatty acid diesters, acctylated glycerol fatty acid monoesters, glycerol fatty acid diesters, lower alcohol fatty acid monoesters, lower alcohol fatty acid diesters, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, un-ionized (b) fatty acids, carnitine fatty acid esters, alkylsulfates, acyl lactylates, mono-acetylated tartaric acid esters of mono- and diglycerides, diacetylated tartaric acid esters of mono- and diglycerdied, succinylated monoglycerides, citric acid esters of mono- and diglycerides, and mixtures thereof, wherein the hydrophilic and hydrophobic surfactants are present in amounts such that upon mixing with an aqueous diluent the composition forms a clear aqueous dispersion having an absorbance of less than about 0.3 at 400 nm, and wherein the composition is free of triglycerides;

(b) providing a hydrophilic therapeutic agent; and (c) administering the dosage form of the absorption enhancing composition and the hydrophilic therapeutic agent to the patient.

157. The method of claim 156, wherein the hydrophilic therapeutic agent is contained in the dosage form of the absorption enhancing composition.

158. The method of claim 157, wherein the hydrophilic therapeutic agent is solubilized, suspended, or partially solubilized and partially suspended, in the dosage form of the absorption enhancing composition.

159. The method of claim 156, wherein the hydrophilic therapeutic agent is provided in a second dosage form separate from the dosage form containing the absorption enhancing composition.

160. The method of claim 159, wherein the step of administering comprises administering the dosage form of the absorption enhancing composition and co-administering the dosage form of the hydrophilic therapeutic agent.

161. The method of claim 156, wherein the dosage form of the absorption enhancing composition is formulated for oral, mucosal, pulmonary, nasal, vaginal, transmembrane, buccal or rectal administration.

162. The method of claim 159, wherein the dosage form of the hydrophilic therapeutic agent is formulated for oral, mucosal, pulmonary, nasal, vaginal, transmembrane, buccal or rectal administration.

163. The method of claim 156, wherein the patient is a mammal.

164. The method of claim 156, wherein the patient is a human.

165. A pharmaceutical system for enhanced absorption of a hydrophilic therapeutic agent in the form of a diluted preconcentrate, the system consisting essentially of:

(a) a dosage form of an absorption enhancing composition, the composition comprising:

(i) at least one hydrophilic surfactant selected from the group consisting of ionized ionizable surfactants, non-ionic hydrophilic surfactants having an HLB value greater than or equal to 10, and combinations thereof, (ii) at least one hydrophobic surfactant selected from the group consisting of hydrophobic (a) alcohols, polyoxyethylene alkylethers, bile acids, glycerol fatty acid monoesters, glycerol fatty acid diesters, acetylated glycerol fatty acid monoesters, acctylated glycerol fatty acid diesters, lower alcohol fatty acid monoesters, lower alcohol fatty acid diestes, polyethylene glycol fatty acid esters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, un-ionized (b) fatty acids, carmitine fatty acid esters, alkylsulfates, acyl lactylates, mono-acetylated tartaric acid esters of mono- and diglycerides, diacetylated tartaric acid esters of mono- and diglycerides, succinylated monoglycerides, citric acid esters of mono- and diglycerides, and mixtures thereof, wherein the hydrophilic aid hydrophobic surfactants are present in amounts such that upon mixing with an aqueous diluent at 100× dilution, the composition forms a clear aqueous dispersion having an absorbance of less than about 0.3 at 400 nm, (iii) a liquid diluent; and (b) a therapeutically effective amount of a hydrophilic therapeutic agent;

wherein the pharmaceutical system is free of triglycerides.

166. A pharmaceutical system for enhancing absorption, or a hydrophilic therapeutic agent in the form of a diluted preconcentrate, the system consisting essentially of:

(a) a dosage form of an absorption enhancing composition, the composition comprising:

(i) at least one hydrophilic surfactant selected from the group consisting of ionized ionizable surfactants, non-ionic hydrophilic surfactants having an HLB value greater than or equal to 10, and combinations thereof, (ii) at least one hydrophobic surfactant selected from the group consisting of hydrophobic (a) alcohols, polyoxyethylene alkylethers, bile acids, glycerol fatty acid monoesters, glycerol fatty acid diesters, acetylated glycerol fatty acid monoesters, acetylated glycerol fatty acid diesters, lower alcohol fatty acid monoesters, lower alcohol fatty acid diesters, polyethylene glycol fatty acid monoesters, polyethylene glycol glycerol fatty acid esters, polypropylene glycol fatty acid esters, polyoxyethylene glycerides, lactic acid derivatives of mono- and diglycerides, propylene glycol diglycerides, sorbitan fatty acid esters, polyoxyethylene sorbitan fatty acid esters, polyoxyethylene-polyoxypropylene block copolymers, transesterified vegetable oils, sugar esters, sugar ethers, sucroglycerides, polyoxyethylene vegetable oils, polyoxyethylene hydrogenated vegetable oils, reaction products of polyols and at least one member of the group consisting of fatty acids, glycerides, vegetable oils, and hydrogenated vegetable oils, and hydrophobic, un-ionized (b) fatty acids, carnitine fatty acid esters, alkylsulfates, acyl lactylates, mono-acetylated tartarie acid esters of mono- and diglycerides, diacetylated tartaric acid esters of mono- and diglycerides, succinylated monoglycerides, citric acid esters of mono- and diglycerides, and mixtures thereof, wherein the hydrophilic and hydrophobic surfactants are present in amounts such that upon mixing with an aqueous diluent at 100× dilution, the composition forms a clear aqueous dispersion having an absorbance of less than about 0.3 at 400 nm, wherein the hydrophilic and hydrophobic surfactants are present in amounts such that upon mixing with an aqueous diluent at 100× dilution, The composition forms a clear aqueous dispersion having an absorbance of less than about 0.3 at 400 nm, (iii) at least one solubilizer, and (iv) a liquid diluent; and (b) a therapeutically effective amount of a hydrophilic therapeutic agent;

wherein the pharmaceutical system is free of triglycerides.

167. The pharmaceutical system of claim 165, wherein the therapeutic agent is provided to the system in the liquid diluent.

168. The pharmaceutical system of claim 165, further comprising an amount of an enzyme inhibiting agent sufficient to at least partially inhibit enzymatic degradation of the hydrophilic therapeutic agent, the enzyme inhibiting agent being solubilized, suspended, or partially solubilized and partially suspended, in the aqueous medium.

169. The pharmaceutical system of claim 166, wherein the therapeutic agent is provided to the system in the liquid diluent.

170. The pharmaceutical system of claim 166, further comprising an amount of an enzyme inhibiting agent sufficient to at least partially inhibit enzymatic degradation of the hydrophilic therapeutic agent, the enzyme inhibiting agent being solubilized, suspended, or partially solubilized and partially suspended, in the aqueous medium.

\* \* \* \* \*

UNITED STATES PATENT AND TRADEMARK OFFICE
CERTIFICATE OF CORRECTION

PATENT NO.    : 6,309,663 B1
DATED         : October 30, 2001
INVENTOR(S)   : Mahesh V. Patel and Feng-Jing Chen It is certified that error appears in the above-identified patent and that said Letters Patent is hereby corrected as shown below:

<u>Title page, Item [54] and Column 1, lines 1-4,</u>
Delete "TRIGLYCERIDE-FREE COMPOSITIONS AND METHODS FOR ENHANCED ABSORPTION OF HYDROPHILIC THERAPEUTIC AGENTS", and insert -- COMPOSITIONS AND METHODS FOR ENHANCED ABSORPTION OF HYDROPHILIC THERAPEUTIC AGENTS --.

Signed and Sealed this

Twenty-fourth Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

<u>Column 50, line 46 to Column 53, line 53,</u>
Replace tables A-E with the following:

-- <u>A: Compositions Having At least Two Hydrophilic Surfactants</u>

| | |
|---|---|
| Sodium taurocholate | 0.18 g |
| Cremophor RH 40 | 0.30 g |
| | |
| Sodium chenodeoxycholate | 0.30 g |
| Tween 80 | 0.50 g |
| | |
| Sodium Sarcocholate | 0.15 g |
| Crovol M-70 | 0.60 g |
| | |
| Sodium lithocholate | 0.30 g |
| Labrasol | 0.55 g |
| | |
| Sodium glycocholate | 0.10 g |
| Tween 20 | 0.50 g |
| | |
| Sodium ursodeoxycholate | 0.30 g |
| Incrocas-35 | 0.50 g |
| | |
| Chenodeoxycholic acid | 0.25 g |
| Cremophor RH 40 | 0.50 g |
| | |
| Cremophor RH 40 | 0.60 g |
| Sodium caprate | 0.10 g |
| | |
| Cremophor RH 40 | 0.50 g |
| Palmitoyl carnitine | 0.20 g |
| | |
| Solulan C-24 | 0.60 g |
| Sodium chenodeoxycholate | 0.25 g |
| | |
| Taurocholate | 0.20 g |
| Egg or Soy lecithin | 0.09 g |
| | |
| Tween 20 | 0.30 g |
| Sodium taurocholate | 0.20 g |
| | |
| Tween 20 | 0.25 g |
| Egg lecithin | 0.15 g |
| | |
| Chenodeoxycholate | 0.18 g |
| $C_{18}$ lysolipid | 0.10 g |
| | |
| Chenodeoxycholate | 0.20 g |
| Oleic acid | 0.10 g |
| | |
| Labrasol | 0.20 g |
| Brij 35 | 0.75 g |

B: Compositions Having One Hydrophilic and One Hydrophobic Surfactant

| | |
|---|---|
| Cremophor EL-P | 0.83 g |
| Peceol | 0.17 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor EL-P | 0.50 g |
| Propylene glycol monocaprate | 0.20 g |
| | |
| Cremophor EL-P | 0.50 g |
| Imwitor 375 | 0.20 g |
| | |
| Cremophor EL-P | 0.50 g |
| Nikkol MGM | 0.18 g |
| | |
| Cremophor RH 40 | 0.50 g |
| Arlacel 186 | 0.10 g |
| | |
| Cremophor RH 40 | 1.53 g |
| Arlacel 186 | 0.38 g |
| HPB cyclodextrin | 0.18 g |
| | |
| Cremophor RH 40 | 0.55 g |
| Capmul MCM | 0.80 g |
| | |
| Cremophor RH 40 | 0.50 g |
| Crodamol (ethyl oleate) | 0.28 g |
| | |
| Cremophor RH 40 | 0.50 g |
| Labrafril | 0.40 g |
| | |
| Cremophor RH 40 | 0.22 g |
| Lauroglycol FCC | 0.20 g |
| | |
| Cremophor RH 40 | 0.60 g |
| Glyceryl monolaurate | 0.20 g |
| | |
| Cremophor RH-40 | 0.43 g |
| Myvacet 9-45 | 0.31 g |
| | |
| Cremophor RH-40 | 0.30 g |
| Peceol | 0.11 g |
| | |
| Cremophor RH40 | 0.50 g |
| Propylene glycol monololeate | 0.20 g |
| | |
| Cremophor RH40 | 0.50 g |
| Softigen 701 | 0.10 g |
| | |
| Cremophor RH40 | 0.50 g |
| Sorbitan monocaprate | 0.25 g |
| | |
| Cremophor RH 60 | 0.54 g |
| Span 80 | 0.26 g |
| | |
| Cremophor RH 40 | 0.70 g |
| Volpo 3 | 0.30 g |
| | |
| Crodet O40 | 0.68 g |
| Plurol Oleique | 0.32 g |
| | |
| Crovol M-70 | 0.61 g |
| Crovol M-40 | 0.12 g |
| | |
| Crovol M-70 | 0.38 g |
| Labrafil | 0.60 g |
| | |
| Crovol M-70 | 0.65 g |
| Imwitor 988 | 0.15 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Crovol M-70 | 0.60 g |
| Linoleic acid | 0.20 g |
| | |
| Emalex C-40 | 0.50 g |
| Gelucire 33/01 | 0.15 g |
| | |
| Glycerox L | 0.73 g |
| Myvacet 9-45 | 0.27 g |
| | |
| Incrocas 35 | 0.65 g |
| Arlacel 186 | 0.12 g |
| | |
| Incrocas 35 | 0.25 g |
| Gelucire 44/14 | 0.15 g |
| | |
| Incrocas 35 | 0.83 g |
| Imwitor 988 | 0.20 g |
| | |
| Incrocas 35 | 0.31 g |
| Labrafil | 0.11 g |
| | |
| Labrasol | 0.83 g |
| Lauroglycol | 0.17 g |
| | |
| Lauroyl carnitine | 0.15 g |
| Imwitor 312 | 0.15 g |
| | |
| Incrocas 35 | 0.50 g |
| Myvacet 9-45 | 0.38 g |
| | |
| Incrocas-35 | 0.50 g |
| Span-20 | 0.15 g |
| | |
| Incrocas 35 | 0.51 g |
| Imwitor 988 | 0.22 g |
| | |
| Kessco PEG 300DL | 0.35 g |
| Gelucire 50/15 | 0.50 g |
| | |
| Kessco PEG 1540DO | 0.65 g |
| Span 80 | 0.12 g |
| | |
| Labrasol | 0.45 g |
| Span-20 | 0.25 g |
| | |
| Myrj 45 | 0.50 g |
| Sorbitan monocaprylate | 0.25 g |
| | |
| Myrj 52 | 0.50 g |
| Imwitor 308 | 0.20 g |
| | |
| Sucrose monolaurate | 0.50 g |
| Capmul MCM | 0.20 g |
| | |
| Nikkol Decaglyn 1-L | 0.55 g |
| Crovol M-40 | 0.33 g |
| | |
| Nikkol Decaglyn 1-0 | 0.65 g |
| Capmul MCM | 0.25 g |
| | |
| Nikkol DHC | 0.67 g |
| Nikkol TMGO-5 | 0.17 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Nikkol BPS-30 | 0.30 g |
| PEG-6 castor oil | 0.15 g |
| Tween 20 | 0.75 g |
| Drewpol 6-1-0 | 0.15 g |
| Tween 20 | 0.34 g |
| Lauroglycol FCC | 0.11 g |
| Tween 20 | 0.58 g |
| Plurol Oleique | 0.21 g |
| Tween 80 | 0.67 g |
| Lauroglycol | 0.17 g |
| Tagat O2 | 0.50 g |
| PGMG-03 | 0.05 g |
| Tagat L2 | 0.68 g |
| Brij 30 | 0.32 g |
| Poloxamer 188 | 0.85 g |
| Labrafil M2125CS | 0.15 g |
| Poloxamer 108 | 0.85 g |
| Capmul GMO-K | 0.15 g |
| Solulan C-24 | 0.58 g |
| Lauroglycol FCC | 0.21 g |

C: Two Hydrophilic Surfactants and One Hydrophobic Surfactant

| | |
|---|---|
| Cremophor EL | 0.30 g |
| Labrasol | 0.30 g |
| Capmul MCM | 0.40 g |
| Cremophor RH-40 | 0.25 g |
| Labrasol | 0.25 g |
| Capmul GMO-K | 0.11 g |
| Cremophor RH 40 | 0.30 g |
| Tween-20 | 0.20 g |
| Nikkol Decaglyn 3-O | 0.50 g |
| Cremophor EL-P | 0.45 g |
| Corvol M-40 | 0.25 g |
| Sodium Docusate | 0.15 g |
| Cremophor RH 40 | 0.65 g |
| Arlacel 186 | 0.15 g |
| Sodium dodecyl sulfate | 0.10 g |
| Cremophor RH 40 | 0.50 g |
| Peceol | 0.20 g |
| Sodium docusate | 0.20 g |
| Sodium Chenodeoxycholate | 0.30 g |
| Cremophor RH 40 | 0.40 g |
| Arlacel 186 | 0.30 g |
| Cremophor RH 40 | 0.41 g |
| Sodium taurocholate | 0.26 g |
| Arlacel 186 | 0.27 g |
| Cremophor RH 40 | 0.50 g |
| Softigen 767 | 0.22 g |
| Arlacel 186 | 0.15 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor RH 40 | 0.40 g |
| Arlacel 186 | 0.40 g |
| Tween 20 | 0.20 g |
| | |
| Cremophor RH 40 | 0.35 g |
| Capmul MCM | 0.30 g |
| Sodium chenodeoxycholate | 0.30 g |
| | |
| Kessco PEG 1000MO | 0.30 g |
| Labrasol | 0.30 g |
| Span 20 | 0.40 g |
| | |
| Polaxamer 188 | 0.65 g |
| Peceol | 0.15 g |
| Sodium dodecyl sulfate | 0.10 g |
| | |
| Sodium taurocholate | 0.17 g |
| Tween 20 | 0.66 g |
| Arlacel 186 | 0.17 g |
| | |
| Sodium taurocholate | 0.17 g |
| Kessco PEG 1000MO | 0.66 g |
| Plurol Oleique | 0.17 g |
| | |
| Sodium taurocholate | 0.15 g |
| Tween 80 | 0.18 g |
| Arlacel 186 | 0.18 g |
| | |
| Taurochenodeoxycholate | 0.15 g |
| Tween 20 | 0.40 g |
| Arlacel 186 | 0.15 g |
| | |
| Chenodeoxycholic acid | 0.25 g |
| Incrocas-35 | 0.30 g |
| Span 20 | 0.20 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor RH 40 | 1.53 g |
| Arlacel 186 | 0.38 g |
| Peceol | 0.38 g |
| HPB beta cyclodextrin | 0.38 g |
| | |
| Cremophor RH 40 | 0.55 g |
| Labrafil M2125 CS | 0.34 g |
| Span 80 | 0.2 g |
| | |
| Cremophor RH 40 | 0.50 g |
| Labrafil M2125 Cs | 0.27 g |
| Crovol M-40 | 0.28 g |

E: Two Hydrophilic and Two Hydrophobic Surfactants

| | |
|---|---|
| Polaxamer 108 | 0.45 g |
| Span 20 | 0.25 g |
| Sodium docusate | 0.15 g |
| Ethyl oleate | 0.15 g |
| | |
| Softigen 767 | 0.45 g |
| Imwitor 742 | 0.25 g |
| Sodium docusate | 0.15 g |
| Ethyl oleate | 0.15 g-- |

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

Column 50, line 46 to Column 53, line 53,
Replace tables A-E with the following:

-- A: Compositions Having At least Two Hydrophilic Surfactants

| | |
|---|---|
| Sodium taurocholate | 0.18 g |
| Cremophor RH 40 | 0.30 g |
| | |
| Sodium chenodeoxycholate | 0.30 g |
| Tween 80 | 0.50 g |
| | |
| Sodium Sarcocholate | 0.15 g |
| Crovol M-70 | 0.60 g |
| | |
| Sodium lithocholate | 0.30 g |
| Labrasol | 0.55 g |
| | |
| Sodium glycocholate | 0.10 g |
| Tween 20 | 0.50 g |
| | |
| Sodium ursodeoxycholate | 0.30 g |
| Incrocas-35 | 0.50 g |
| | |
| Chenodeoxycholic acid | 0.25 g |
| Cremophor RH 40 | 0.50 g |
| | |
| Cremophor RH 40 | 0.60 g |
| Sodium caprate | 0.10 g |
| | |
| Cremophor RH 40 | 0.50 g |
| Palmitoyl carnitine | 0.20 g |
| | |
| Solulan C-24 | 0.60 g |
| Sodium chenodeoxycholate | 0.25 g |
| | |
| Taurocholate | 0.20 g |
| Egg or Soy lecithin | 0.09 g |
| | |
| Tween 20 | 0.30 g |
| Sodium taurocholate | 0.20 g |
| | |
| Tween 20 | 0.25 g |
| Egg lecithin | 0.15 g |
| | |
| Chenodeoxycholate | 0.18 g |
| $C_{18}$ lysolipid | 0.10 g |
| | |
| Chenodeoxycholate | 0.20 g |
| Oleic acid | 0.10 g |
| | |
| Labrasol | 0.20 g |
| Brij 35 | 0.75 g |

B: Compositions Having One Hydrophilic and One Hydrophobic Surfactant

| | |
|---|---|
| Cremophor EL-P | 0.83 g |
| Peceol | 0.17 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor EL-P | 0.50 g |
| Propylene glycol monocaprate | 0.20 g |
| | |
| Cremophor EL-P | 0.50 g |
| Imwitor 375 | 0.20 g |
| | |
| Cremophor EL-P | 0.50 g |
| Nikkol MGM | 0.18 g |
| | |
| Cremophor RH 40 | 0.50 g |
| Arlacel 186 | 0.10 g |
| | |
| Cremophor RH 40 | 1.53 g |
| Arlacel 186 | 0.38 g |
| HPB cyclodextrin | 0.18 g |
| | |
| Cremophor RH 40 | 0.55 g |
| Capmul MCM | 0.80 g |
| | |
| Cremophor RH 40 | 0.50 g |
| Crodamol (ethyl oleate) | 0.28 g |
| | |
| Cremophor RH 40 | 0.50 g |
| Labrafril | 0.40 g |
| | |
| Cremophor RH 40 | 0.22 g |
| Lauroglycol FCC | 0.20 g |
| | |
| Cremophor RH 40 | 0.60 g |
| Glyceryl monolaurate | 0.20 g |
| | |
| Cremophor RH-40 | 0.43 g |
| Myvacet 9-45 | 0.31 g |
| | |
| Cremophor RH-40 | 0.30 g |
| Peceol | 0.11 g |
| | |
| Cremophor RH40 | 0.50 g |
| Propylene glycol monololeate | 0.20 g |
| | |
| Cremophor RH40 | 0.50 g |
| Softigen 701 | 0.10 g |
| | |
| Cremophor RH40 | 0.50 g |
| Sorbitan monocaprate | 0.25 g |
| | |
| Cremophor RH 60 | 0.54 g |
| Span 80 | 0.26 g |
| | |
| Cremophor RH 40 | 0.70 g |
| Volpo 3 | 0.30 g |
| | |
| Crodet O40 | 0.68 g |
| Plurol Oleique | 0.32 g |
| | |
| Crovol M-70 | 0.61 g |
| Crovol M-40 | 0.12 g |
| | |
| Crovol M-70 | 0.38 g |
| Labrafil | 0.60 g |
| | |
| Crovol M-70 | 0.65 g |
| Imwitor 988 | 0.15 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Crovol M-70 | 0.60 g |
| Linoleic acid | 0.20 g |
| | |
| Emalex C-40 | 0.50 g |
| Gelucire 33/01 | 0.15 g |
| | |
| Glycerox L | 0.73 g |
| Myvacet 9-45 | 0.27 g |
| | |
| Incrocas 35 | 0.65 g |
| Arlacel 186 | 0.12 g |
| | |
| Incrocas 35 | 0.25 g |
| Gelucire 44/14 | 0.15 g |
| | |
| Incrocas 35 | 0.83 g |
| Imwitor 988 | 0.20 g |
| | |
| Incrocas 35 | 0.31 g |
| Labrafil | 0.11 g |
| | |
| Labrasol | 0.83 g |
| Lauroglycol | 0.17 g |
| | |
| Lauroyl carnitine | 0.15 g |
| Imwitor 312 | 0.15 g |
| | |
| Incrocas 35 | 0.50 g |
| Myvacet 9-45 | 0.38 g |
| | |
| Incrocas-35 | 0.50 g |
| Span-20 | 0.15 g |
| | |
| Incrocas 35 | 0.51 g |
| Imwitor 988 | 0.22 g |
| | |
| Kessco PEG 300DL | 0.35 g |
| Gelucire 50/15 | 0.50 g |
| | |
| Kessco PEG 1540DO | 0.65 g |
| Span 80 | 0.12 g |
| | |
| Labrasol | 0.45 g |
| Span-20 | 0.25 g |
| | |
| Myrj 45 | 0.50 g |
| Sorbitan monocaprylate | 0.25 g |
| | |
| Myrj 52 | 0.50 g |
| Imwitor 308 | 0.20 g |
| | |
| Sucrose monolaurate | 0.50 g |
| Capmul MCM | 0.20 g |
| | |
| Nikkol Decaglyn 1-L | 0.55 g |
| Crovol M-40 | 0.33 g |
| | |
| Nikkol Decaglyn 1-0 | 0.65 g |
| Capmul MCM | 0.25 g |
| | |
| Nikkol DHC | 0.67 g |
| Nikkol TMGO-5 | 0.17 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Nikkol BPS-30 | 0.30 g |
| PEG-6 castor oil | 0.15 g |
| | |
| Tween 20 | 0.75 g |
| Drewpol 6-1-0 | 0.15 g |
| | |
| Tween 20 | 0.34 g |
| Lauroglycol FCC | 0.11 g |
| | |
| Tween 20 | 0.58 g |
| Plurol Oleique | 0.21 g |
| | |
| Tween 80 | 0.67 g |
| Lauroglycol | 0.17 g |
| | |
| Tagat O2 | 0.50 g |
| PGMG-03 | 0.05 g |
| | |
| Tagat L2 | 0.68 g |
| Brij 30 | 0.32 g |
| | |
| Poloxamer 188 | 0.85 g |
| Labrafil M2125CS | 0.15 g |
| | |
| Poloxamer 108 | 0.85 g |
| Capmul GMO-K | 0.15 g |
| | |
| Solulan C-24 | 0.58 g |
| Lauroglycol FCC | 0.21 g |

C: Two Hydrophilic Surfactants and One Hydrophobic Surfactant

| | |
|---|---|
| Cremophor EL | 0.30 g |
| Labrasol | 0.30 g |
| Capmul MCM | 0.40 g |
| | |
| Cremophor RH-40 | 0.25 g |
| Labrasol | 0.25 g |
| Capmul GMO-K | 0.11 g |
| | |
| Cremophor RH 40 | 0.30 g |
| Tween-20 | 0.20 g |
| Nikkol Decaglyn 3-O | 0.50 g |
| | |
| Cremophor EL-P | 0.45 g |
| Corvol M-40 | 0.25 g |
| Sodium Docusate | 0.15 g |
| | |
| Cremophor RH 40 | 0.65 g |
| Arlacel 186 | 0.15 g |
| Sodium dodecyl sulfate | 0.10 g |
| | |
| Cremophor RH 40 | 0.50 g |
| Peceol | 0.20 g |
| Sodium docusate | 0.20 g |
| | |
| Sodium Chenodeoxycholate | 0.30 g |
| Cremophor RH 40 | 0.40 g |
| Arlacel 186 | 0.30 g |
| | |
| Cremophor RH 40 | 0.41 g |
| Sodium taurocholate | 0.26 g |
| Arlacel 186 | 0.27 g |
| | |
| Cremophor RH 40 | 0.50 g |
| Softigen 767 | 0.22 g |
| Arlacel 186 | 0.15 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor RH 40 | 0.40 g |
| Arlacel 186 | 0.40 g |
| Tween 20 | 0.20 g |
| | |
| Cremophor RH 40 | 0.35 g |
| Capmul MCM | 0.30 g |
| Sodium chenodeoxycholate | 0.30 g |
| | |
| Kessco PEG 1000MO | 0.30 g |
| Labrasol | 0.30 g |
| Span 20 | 0.40 g |
| | |
| Polaxamer 188 | 0.65 g |
| Peceol | 0.15 g |
| Sodium dodecyl sulfate | 0.10 g |
| | |
| Sodium taurocholate | 0.17 g |
| Tween 20 | 0.66 g |
| Arlacel 186 | 0.17 g |
| | |
| Sodium taurocholate | 0.17 g |
| Kessco PEG 1000MO | 0.66 g |
| Plurol Oleique | 0.17 g |
| | |
| Sodium taurocholate | 0.15 g |
| Tween 80 | 0.18 g |
| Arlacel 186 | 0.18 g |
| | |
| Taurochenodeoxycholate | 0.15 g |
| Tween 20 | 0.40 g |
| Arlacel 186 | 0.15 g |
| | |
| Chenodeoxycholic acid | 0.25 g |
| Incrocas-35 | 0.30 g |
| Span 20 | 0.20 g |
| | |
| Saurcocholate | 0.20 g |
| Cremophor RH 40 | 0.40 g |
| Arlacel 186 | 0.20 g |
| | |
| Lithocholate | 0.25 g |
| Incrocas-35 | 0.40 g |
| Myvacet 9-45 | 0.30 g |
| | |
| Tagat L2 | 0.45 g |
| Crovol A-40 | 0.25 g |
| Sodium docusate | 0.15 g |
| | |
| Tween-20 | 0.30 g |
| Arlacel 186 | 0.20 g |
| Sodium chenodeoxycholate | 0.25 g |
| | |
| Cremophor RH 40 | 0.40 g |
| Tween-20 | 0.25 g |
| Sodium caprate | 0.25 g |
| | |
| Cremophor RH40 | 0.40 g |
| Lauric acid | 0.20 g |
| Incrocas-35 | 0.30 g |

D: One Hydrophilic and Two Hydrophobic Surfactants

| | |
|---|---|
| Cremophor RH 40 | 0.50 g |
| Labrafil M2125CS | 0.27 g |
| Crovol M-40 | 0.28 g |

UNITED STATES PATENT AND TRADEMARK OFFICE
CERTIFICATE OF CORRECTION

PATENT NO. : 6,309,663 B1
DATED : October 30, 2001
INVENTOR(S) : Mahesh V. Patel and Feng-Jing Chen It is certified that error appears in the above-identified patent and that said Letters Patent is hereby corrected as shown below:

| | |
|---|---|
| Cremophor RH 40 | 1.53 g |
| Arlacel 186 | 0.38 g |
| Peceol | 0.38 g |
| HPB beta cyclodextrin | 0.38 g |
| | |
| Cremophor RH 40 | 0.55 g |
| Labrafil M2125 CS | 0.34 g |
| Span 80 | 0.2 g |
| | |
| Cremophor RH 40 | 0.50 g |
| Labrafil M2125 Cs | 0.27 g |
| Crovol M-40 | 0.28 g |

E: Two Hydrophilic and Two Hydrophobic Surfactants

| | |
|---|---|
| Polaxamer 108 | 0.45 g |
| Span 20 | 0.25 g |
| Sodium docusate | 0.15 g |
| Ethyl oleate | 0.15 g |
| | |
| Softigen 767 | 0.45 g |
| Imwitor 742 | 0.25 g |
| Sodium docusate | 0.15 g |
| Ethyl oleate | 0.15 g-- |

This certificate supersedes Certificate of Correction issued January 7, 2003.

Signed and Sealed this

First Day of April, 2003

JAMES E. ROGAN
*Director of the United States Patent and Trademark Office*